(12) United States Patent
Chao et al.

(10) Patent No.: US 8,754,223 B2
(45) Date of Patent: *Jun. 17, 2014

(54) CRYSTALLINE FORM OF A BIPHENYL COMPOUND

(71) Applicants: Robert S. Chao, Santa Clara, CA (US); Miroslav Rapta, San Carlos, CA (US); Pierre-Jean Colson, San Francisco, CA (US)

(72) Inventors: Robert S. Chao, Santa Clara, CA (US); Miroslav Rapta, San Carlos, CA (US); Pierre-Jean Colson, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,708

(22) Filed: Jun. 5, 2013

(65) Prior Publication Data

US 2013/0289281 A1  Oct. 31, 2013

Related U.S. Application Data

(63) Continuation of application No. 13/328,366, filed on Dec. 16, 2011, now Pat. No. 8,476,299, which is a continuation of application No. 12/369,605, filed on Feb. 11, 2009, now Pat. No. 8,101,766, which is a continuation of application No. 11/204,065, filed on Aug. 15, 2005, now Pat. No. 7,521,558.

(60) Provisional application No. 60/601,805, filed on Aug. 16, 2004.

(51) Int. Cl.
*C07D 215/38* (2006.01)

(52) U.S. Cl.
USPC .......................................... 546/157

(58) Field of Classification Search
USPC .......................................... 546/157; 514/312
See application file for complete search history.

(56) References Cited

U.S. PATENT DOCUMENTS

| | | | |
|---|---|---|---|
| 6,653,323 B2 | 11/2003 | Moran et al. | |
| 7,141,671 B2 | 11/2006 | Mammen et al. | |
| 7,320,990 B2 | 1/2008 | Chao et al. | |
| 7,345,175 B2 | 3/2008 | Mammen et al. | |
| 7,355,046 B2 | 4/2008 | Mammen et al. | |
| 7,507,751 B2 | 3/2009 | Mammen et al. | |
| 7,521,558 B2 * | 4/2009 | Chao et al. | 546/135 |
| 7,521,561 B2 | 4/2009 | Mammen et al. | |
| 7,524,959 B2 | 4/2009 | Mammen et al. | |
| 8,101,766 B2 * | 1/2012 | Chao et al. | 546/156 |
| 8,476,299 B2 * | 7/2013 | Chao et al. | 514/312 |
| 2003/0018019 A1 | 1/2003 | Meade et al. | |
| 2004/0209860 A1 | 10/2004 | Mammen et al. | |
| 2004/0209915 A1 | 10/2004 | Mammen et al. | |
| 2005/0025718 A1 | 2/2005 | Meade et al. | |

FOREIGN PATENT DOCUMENTS

| | | |
|---|---|---|
| WO | 99/64031 A1 | 12/1999 |
| WO | 01/42212 A1 | 6/2001 |
| WO | 01/42213 A1 | 6/2001 |
| WO | 20041074276 A1 | 9/2004 |

OTHER PUBLICATIONS

Berge et al., "Pharmaceutical Salts", Journal of Pharmaceutical Sciences, vol. 66, No. 1, pp. 1-19, Jan. 1977.
Gould, "Salt Selection for Basic Drugs", International Journal of Pharmaceutics, vol. 33, pp. 201-217, 1986.
Li et al., "Relationship Between Physical Properties and Crystal Structures of Chiral Drugs", American Chemical Society and American Pharmaceutical Association, vol. 86, No. 10, pp. 1073-1078, Oct. 1997.
International Search Report for PCT/US2005/029013.
Written Opinion of the International Searching Authority for PCT/US2005/029013.
Office Action for U.S. Appl. No. 11/204,065 dated Oct. 20, 2008.
Office Action for U.S. Appl. No. 12/369,605 dated Jun. 7, 2011.
Reference Farmacia 19 edicion TOMO 2, pp. 2226-2235 (not in English).

* cited by examiner

*Primary Examiner* — D M Seaman
(74) *Attorney, Agent, or Firm* — Jeffrey A. Hagenah

(57) ABSTRACT

The invention provides a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl) ethyl]piperidin-4-yl ester or a solvate thereof. This invention also provides pharmaceutical compositions comprising such a salt or prepared using such a salt; processes and intermediates for preparing such a salt; and methods of using such a salt to treat a pulmonary disorder.

5 Claims, 4 Drawing Sheets

CRYSTALLINE FORM OF A BIPHENYL COMPOUND

CROSS-REFERENCE TO RELATED APPLICATIONS

This application is a continuation of U.S. application Ser. No. 13/328,386, filed on Dec. 16, 2011; which application is a continuation of U.S. application Ser. No. 12/369,605, filed on Feb. 11, 2009 (now U.S. Pat. No. 8,101,766 B2); which application is a continuation of U.S. application Ser. No. 11/204,065, filed on Aug. 15, 2005 (now U.S. Pat. No. 7,521,558 B2); which application claims the benefit of U.S. Provisional Application No. 60/601,805, filed on Aug. 16, 2004; the entire disclosures of which are incorporated herein by reference in their entirety.

BACKGROUND OF THE INVENTION

1. Field of the Invention

The present invention relates to novel crystalline 1,2-ethanedisulfonic acid salts of a biphenyl compound which are expected to be useful as therapeutic agents for treating pulmonary disorders. This invention also relates to pharmaceutical compositions comprising such crystalline compounds or prepared from such crystalline compounds, processes and intermediates for preparing such crystalline compounds and methods of using such crystalline compounds to treat a pulmonary disorder.

2. State of the Art

Commonly-assigned U.S. patent application Ser. No. 10/779,157, filed on Feb. 13, 2004, disclose novel biphenyl compounds that are useful as therapeutic agents for treating pulmonary disorders, such as chronic obstructive pulmonary disease (COPD) and asthma. In particular, the compound, biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is specifically disclosed in these applications as possessing both muscarinic antagonist and $\beta_2$ adrenergic receptor agonist activity. The chemical structure of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is represented by formula I:

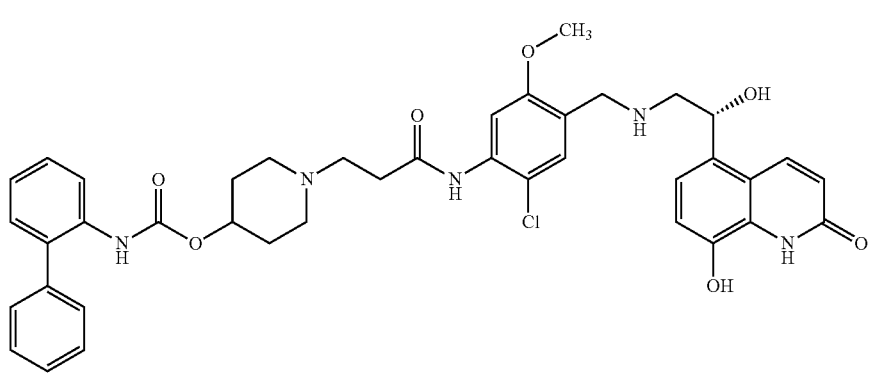

I

Therapeutic agents useful for treating pulmonary disorders are advantageously administered directly into the respiratory tract by inhalation. In this regard, several types of pharmaceutical inhalation devices have been developed for administering therapeutic agents by inhalation including dry powder inhalers (DPI), metered-dose inhalers (MDI) and nebulizer inhalers. When preparing pharmaceutical compositions and formulations for use in such devices, it is highly desirable to have a crystalline form of the therapeutic agent that is neither hygroscopic nor deliquescent and which has a relatively high melting point (i.e. greater than about 150° C.) thereby allowing the material to be micronized without significant decomposition or loss of crystallinity.

No crystalline salt forms of the compound of formula I have been reported previously. Accordingly, a need exists for a stable, non-deliquescent crystalline salt form of the compound of formula I which has an acceptable level of hygroscopicity and a relatively high melting point.

SUMMARY OF THE INVENTION

The present invention provides crystalline 1,2-ethanedisulfonic acid salts of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

Surprisingly, such crystalline 1,2-ethanedisulfonic acid salts of the compound of formula I have been found not to be deliquescent, even when exposed to atmospheric moisture. Additionally, such crystalline salts have an acceptable level of hygroscopicity and a very high melting point, e.g., greater than about 215° C. In a particular embodiment, a crystalline salt of the present invention has a melting point greater than about 230° C.

Among other uses, a crystalline 1,2-ethanedisulfonic acid salt of the compound of formula I is useful for preparing pharmaceutical compositions which are expected to be useful for treating pulmonary disorders. Accordingly, in another of its composition aspects, the present invention provides a pharmaceutical composition comprising a pharmaceutically acceptable carrier and a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

In a particular embodiment, the pharmaceutical composition of this invention further comprises a steroidal anti-inflammatory agent, such as a cortecosteroid; or a phosphodiesterase-4 inhibitor; or a combination thereof.

In another embodiment, this invention provides a pharmaceutical composition comprising an aqueous isotonic saline solution comprising a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, wherein the solution has a pH in the range of from about 4 to about 6.

In yet another embodiment, this invention provides a combination comprising:

(a) a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof; and (b) a steroidal anti-inflammatory agent.

The compound of formula I has both muscarinic antagonist and $\beta_2$ adrenergic receptor agonist activity. Accordingly, a 1,2-ethanedisulfonic acid salt of this invention is expected to be useful as a therapeutic agent for treating pulmonary disorders, such as asthma and chronic obstructive pulmonary disease.

Accordingly, in one of its method aspects, this invention provides a method for treating a pulmonary disorder, the method comprising administering to a patient in need of treatment a therapeutically effective amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

Additionally, in another of its method aspects, this invention provides a method of producing bronchodilation in a patient, the method comprising administering by inhalation to the patient a bronchodilation-producing amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]-piperidin-4-yl ester or a solvate thereof.

This invention also provides a method of treating chronic obstructive pulmonary disease or asthma, the method comprising administering to a patient in need of treatment a therapeutically effective amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

This invention is also directed to processes for preparing a crystalline 1,2-ethanedisulfonic acid salt of the compound of formula I. Accordingly, in another of its method aspects, this invention provides a process for preparing a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof; the process comprising contacting biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester with 1,2-ethanedisulfonic acid.

In yet another of its method aspects, this invention provides a process for preparing a crystalline 1,2-ethanedisulfonic acid salt of a compound of formula I, the process comprising:

(a) contacting a compound of formula II:

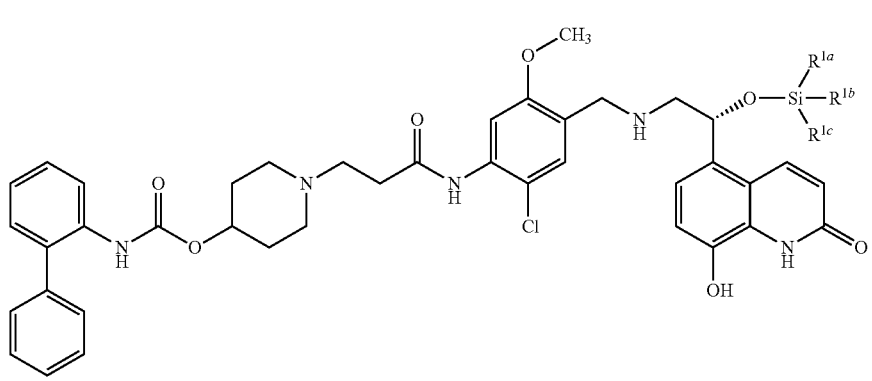

wherein $R^{1a}$, $R^{1b}$ and $R^{1c}$ are independently selected from $C_{1-4}$ alkyl, phenyl, —$C_{1-4}$ alkyl-(phenyl), or one of $R^{1a}$, $R^{1b}$ and $R^{1c}$ is —O—($C_{1-4}$alkyl); with fluoride ion; and (b) contacting the product from step (b) with 1,2-ethanedisulfonic acid or a hydrate thereof; to form a crystalline 1,2-ethanedisulfonic acid salt of a compound of formula I, wherein step (a) and (b) are conducted in the same reaction vessel without isolation of the product of step (a).

In another of its method aspects, this invention provides a process for preparing a crystalline 1,2-ethanedisulfonic acid salt of a compound of formula I having a melting point greater than about 230° C., the process comprising adding a seed crystal of a crystalline 1,2-ethanedisulfonic acid salt of a compound of formula I to a solution comprising a 1,2-ethanedisulfonic acid salt of a compound of formula I dissolved in an inert diluent, wherein the seed crystal has a melting point greater than about 230° C.

This process can also be used to recrystallize a crystalline 1,2-ethanedisulfonic acid salt of a compound of formula I to provide a crystalline form having a melting point greater than about 230° C. Accordingly, the invention further provides a process for preparing a crystalline 1,2-ethanedisulfonic acid salt of a compound of formula I having a melting point greater than about 230° C., the process comprising:

(a) dissolving a crystalline 1,2-ethanedisulfonic acid salt of a compound of formula I in an inert diluent at a first temperature;

(b) cooling the product of step (a) to a second temperature; and (c) adding a seed crystal of a 1,2-ethanedisulfonic acid salt of a compound of formula I;

wherein the seed crystal has a melting point higher than about 230° C., the first temperature is a temperature sufficient to dissolve the 1,2-ethanedisulfonic acid salt, and the second temperature is below a temperature at which the seed crystal completely dissolves when added to the product of step (b).

Additionally, this invention is directed to a process for purifying biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester; the process comprising forming a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester. This invention is also directed to the products prepared by the processes described herein.

This invention is also directed to a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof for use in therapy or as a medicament.

Additionally, this invention is directed to the use of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof for the manufacture of a medicament; especially for the manufacture of a medicament for the treatment of a pulmonary disorder.

This invention is also directed to the use of:

(a) a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof; and (b) a steroidal anti-inflammatory agent;

in the manufacture of a medicament for the treatment of a pulmonary disorder.

This invention is also directed to a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof, in micronized form; and to pharmaceutical compositions comprising a pharmaceutically acceptable carrier and a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]-piperidin-4-yl ester or a solvate thereof, in micronized form.

BRIEF DESCRIPTION OF THE DRAWINGS

Various aspects of the present invention are illustrated by reference to the accompanying drawings.

DETAILED DESCRIPTION OF THE INVENTION

Figure 1:
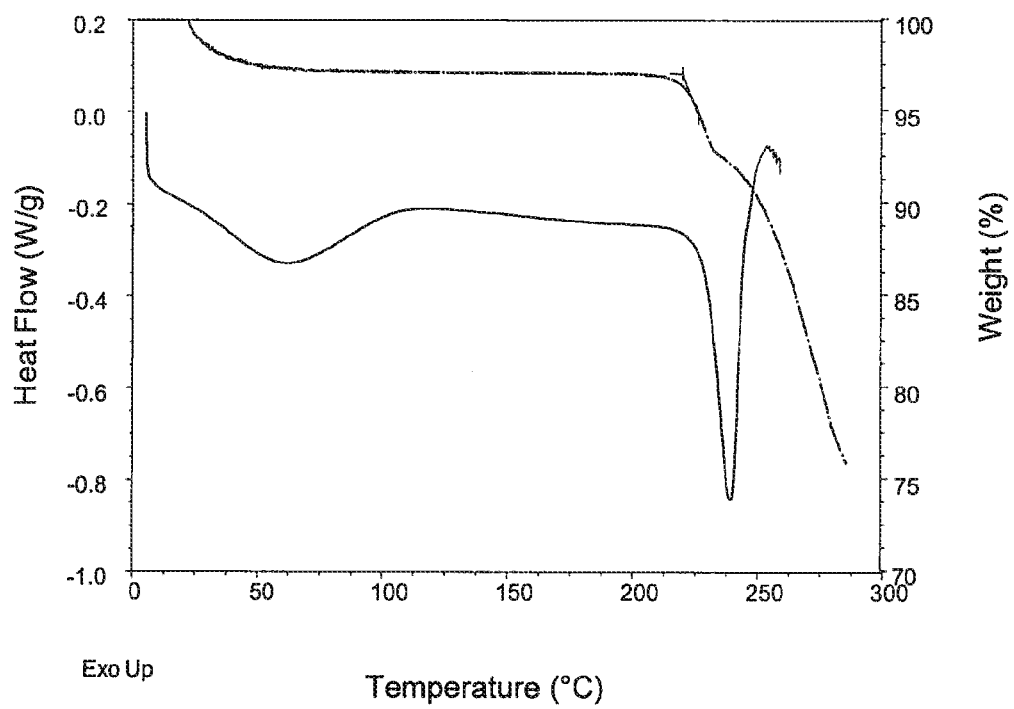
FIG. 1 shows a differential scanning calorimetry (DSC) trace and a thermal gravimetric analysis (TGA) trace and FIG. 2 shows a DSC trace for samples of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention.

This invention provides crystalline 1,2-ethanedisulfonic acid salts of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. The active therapeutic agent in these salts (i.e., the compound of formula I) contains one chiral center having the (R) configuration. However, it will be understood by those skilled in the art that minor amounts of the (S) stereoisomer may be present in the compositions of this invention unless otherwise indicated, provided that any utility of the composition as a whole is not eliminated by the presence of such an isomer.

The compound of formula I has been named using the commercially-available AutoNom software (MDL, San Leandro, Calif.). Additionally, 1,2-ethanedisulfonic acid salts are also sometimes referred to as edisylate salts or edisitate salts.

DEFINITIONS

When describing the compounds, compositions, methods and processes of this invention, the following terms have the following meanings unless otherwise indicated.

The term "melting point" as used herein means the temperature at which the maximum endothermic heat flow is observed by differential scanning calorimetry.

The term "micronized form" means a form of particles in which at least about 90% of the particles have a diameter of less than about 10 µm.

The term "solvate" means a complex or aggregate formed by one or more molecules of a solute, i.e. a 1,2-ethanedisulfonic acid salt of the compound of formula I, and one or more molecules of a solvent. Such solvates typically have a substantially fixed molar ratio of solute and solvent. This term also includes clathrates, including clathrates with water. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The term "unit dosage form" refers to a physically discrete unit suitable for dosing a patient, i.e., each unit containing a predetermined quantity of a salt of the invention calculated to produce the desired therapeutic effect either alone or in combination with one or more additional units. For example, such unit dosage forms may be dry powder inhaler capsules, a metered dose from a metered dose inhaler, capsules, tablets, pills, and the like.

1,2-Ethanedisulfonic Acid Salts of the Invention

A crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention can be prepared from biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester and 1,2-ethanedisulfonic acid or a hydrate thereof.

A 1,2-ethanedisulfonic acid salt of this invention typically contains between about 0.90 and about 1.10 molar equivalents of 1,2-ethanedisulfonic acid per molar equivalent of the compound of formula I; including between about 0.95 and about 1.05 molar equivalents of 1,2-ethanedisulfonic acid per molar equivalent of the compound of formula I. In a particular embodiment, the 1,2-ethanedisulfonic acid salt of this invention contains about 1 molar equivalent of 1,2-ethanedisulfonic acid per molar equivalent of the compound of formula I.

The molar ratio of 1,2-ethanedisulfonic acid to biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester can be readily determined by various methods available to those skilled in the art. For example, such molar ratios can be readily determined by $^1$H NMR. Alternatively, elemental analysis and HPLC methods can be used to determine the molar ratio.

The biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]-piperidin-4-yl ester employed in this invention can be readily prepared from commercially available starting materials and reagents using the procedures described in the Examples below; or using the procedures described in the commonly-assigned U.S. application described in the Background section of this application.

1,2-Ethanedisulfonic acid is commercially available from, for example, Alfa Chemicals Ltd., Berkshire, UK. In one embodiment, the 1,2-ethanedisulfonic acid employed in preparing the salts of this invention is a dihydrate. In a particular embodiment, the 1,2-ethanedisulfonic acid dihydrate has a purity greater than or equal to 97% (as determined by HPLC). If desired, the 1,2-disulfonic acid dihydrate employed in this invention can be recrystallized from, for example, acetic acid and acetic anhydride prior to use.

To prepare a crystalline salt of this invention, the biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is typically contacted with about 0.75 to about 1.3 molar equivalents of 1,2-ethanedisulfonic acid or a hydrate thereof. Generally, this reaction is conducted in an inert diluent at a temperature ranging from about 0° C., to about 60° C.; including about 20° C. to about 55° C., such as about 25° C. to about 50° C. Suitable inert diluents for this reaction include, but are not limited to, methanol, ethanol, isopropanol, isobutanol, ethyl acetate, dichloromethane and the like optionally containing water. In a particular embodiment, a solution of 1,2-ethanedisulfonic acid dihydrate in ethanol is added to about a five times larger volume of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester in a mixture of isopropanol and dichloromethane (64:1). In other particular embodiments, the solution of 1,2-ethanedisulfonic acid dihydrate includes water or ethanol as the diluent and the biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester solution includes isopropanol or ethanol as the diluent.

Alternatively, a crystalline 1,2-ethanedisulfonic acid salt of a compound of formula I can be prepared by contacting a silyl-protected derivative of the compound of formula I (i.e., a compound of formula II) with a source of fluoride ion and then, in the same reaction vessel, contacting the product with 1,2-ethanedisulfonic acid or a hydrate thereof. In a particular embodiment, the silyl-protecting group is a tert-butyldimethylsilyl group. Other suitable silyl-protecting groups include tert-butyldiphenylsilyl, diphenylmethylsilyl, di-tert-butylmethylsilyl, tert-butoxydiphenylsilyl and the like. The source of fluoride ion used in this process can be any reagent containing or comprising fluoride ion or hydrogen fluoride. In a particular embodiment, the source of fluoride ion is triethylamine trihydrofluoride. Other suitable sources of fluoride ion include tetrabutylammonium fluoride, potassium fluoride with 18-crown-6, hydrogen fluoride, pyridine hydrofluoride, and the like.

Generally, this process is conducted in an inert diluent at a temperature ranging from about 0° C. to about 50° C.; including about 20° C. to about 35° C., such as about 25° C. to about 30° C. Suitable inert diluents for this reaction include, but are not limited to, dichloromethane, methanol and mixtures thereof. In a particular embodiment, a solution of biphenyl-2-ylcarbamic acid 1-[2-(4-{[(R)-2-(tert-butyldimethylsilanyloxy)-2-(8-hydroxy-2-oxo-1,2-dihydroquinolin-5-yl)ethylamino]methyl}-2-chloro-5-methoxyphenylcarbamoyl)ethyl]piperidin-4-yl ester is contacted with about 2.5 to about 3.0 molar equivalents of triethylamine trihydrofluoride dichloromethane at ambient temperature for about 12 to 24 hours or until removal of the silyl group is substantially complete. To the resulting solution, without isolation of the reaction product, is added about 0.9 to about 1.1 molar equivalents of 1,2-ethanedisulfonic acid dihydrate in methanol and this mixture is heated at about 25° C. to about 35° C. for about 2 to about 6 hours. Upon completion of the reaction, a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is isolated from the reaction mixture by any conventional means, such as precipitation, concentration, centrifugation and the like.

Optionally, a crystalline 1,2-ethanedisulfonic acid salt of this invention can be further purified by stirring or slurring the salt in isopropanol containing about 15% to about 25%, including about 20%, water by volume. In a particular embodiment, about 10 mL of the isopropanol/water mixture is employed per gram of the 1,2-ethanedisulfonic acid salt.

A process of preparing a crystalline 1,2-ethanedisulfonic acid salt of this invention can optionally include the use of a seed crystal to produce predominately a particular crystalline salt. For example, by using a seed crystal of a higher melting crystalline salt (i.e., greater than about 230° C.), a crystalline 1,2-ethanedisulfonic acid salt of a compound of formula I can be prepared having essentially the same melting point as the seed crystal. Such seed crystals can be used when initially forming the crystalline salt or they can be used to recrystallize a crystalline or partially crystalline salt.

Typically, seed crystals are prepared at small scale by slow crystallization without stirring and without applying cooling. By way of illustration, to obtain seed crystals, the crystalline salt is typically dissolved in an inert diluent at a temperature sufficient to provide dissolution. Generally, in the initial process of obtaining seed crystals, a small quantity, typically less than 10 g, including less than 5 g, such as less than 1 g, of the crystalline salt is used. In a particular embodiment, methanol containing about 12% to about 20% water, including about 13% to about 15% water, is used as the diluent at a temperature ranging from about 60° C. to about 70° C., such as about 60° C. to about 65° C. The solution is allowed to cool to room temperature. After about 1 day to about 3 days, the resulting crystals are isolated by filtration or other conventional means. Alternatively, seed crystals may be obtain from a previous preparation of crystalline material.

In the recrystallization process using seed crystals, a crystalline 1,2-ethanedisulfonic acid salt of this invention is dissolved in an inert diluent as in the process of obtaining seed crystals, typically methanol containing 15% water, at a temperature ranging from about 60° C. to about 65° C. The solution is allowed to cool to a temperature at which the seed crystals do not dissolve, for example to a temperature in the range of from about 30° C. to about 40° C., and then seed crystals are added. Typically, the ratio of the weight of seed crystals to the weight of crystalline salt in the solution is between about 1:5 and about 1:35. The solution is cooled to a temperature at which crystallization occurs, for example, to about 20° C. and stirred for about 2 hours to about 24 hours. The resulting crystals are isolated by conventional means. To obtain sufficient seed crystals to prepare large batches of material, the recrystallization process can be performed successively using the crystals obtained by a first recrystallization as the seed crystals for a subsequent recrystallization step. It will be appreciated that the specific temperatures at which the steps of the recrystallization process are performed are selected depending on the character of the diluent and the concentration of the crystalline salt in the diluent. Additionally, the recrystallization process can be conducted using either evaporation or an anti-solvent to facilitate crystallization instead of cooling.

Among other advantages, it has been discovered that forming a crystalline 1,2-ethanedisulfonic acid salt of the compound of formula I is useful for purifying the compound of formula I. Generally, a crystalline 1,2-ethanedisulfonic acid salt of this invention has a purity greater than 95%; and typically greater than 98%, as determined by high performance liquid chromatography.

The crystalline 1,2-ethanedisulfonic acid salt of the present invention is characterized by a very high melting point as evidenced by differential scanning calorimetry (DSC) traces which exhibit a peak in endothermic heat flow in the range of about 215° C. to about 240° C. It has been observed that the melting point temperature of the crystalline salt is dependent on the process by which the crystalline salt was formed. The seed crystals formed by slow crystallization without stirring and without applied cooling exhibit melting points higher than about 230° C. Crystalline salts formed by a process including recrystallization with such seed crystals typically exhibit melting points in the range of about 230° C. to about 245° C., as shown, for example, in FIG. 1. Crystalline salts formed without a seed crystal having a melting point above about 230° C. typically exhibit melting points in the range of about 215° C. to about 229° C., as shown for example in FIG. 2. In particular embodiments, therefore, the invention provides crystalline 1,2-ethanedisulfonic acid salts of the compound of formula I having a DSC trace in the temperature range above about 200° C. that is substantially in accordance with the trace shown in FIG. 1 or with that shown in FIG. 2.

Figure 3:
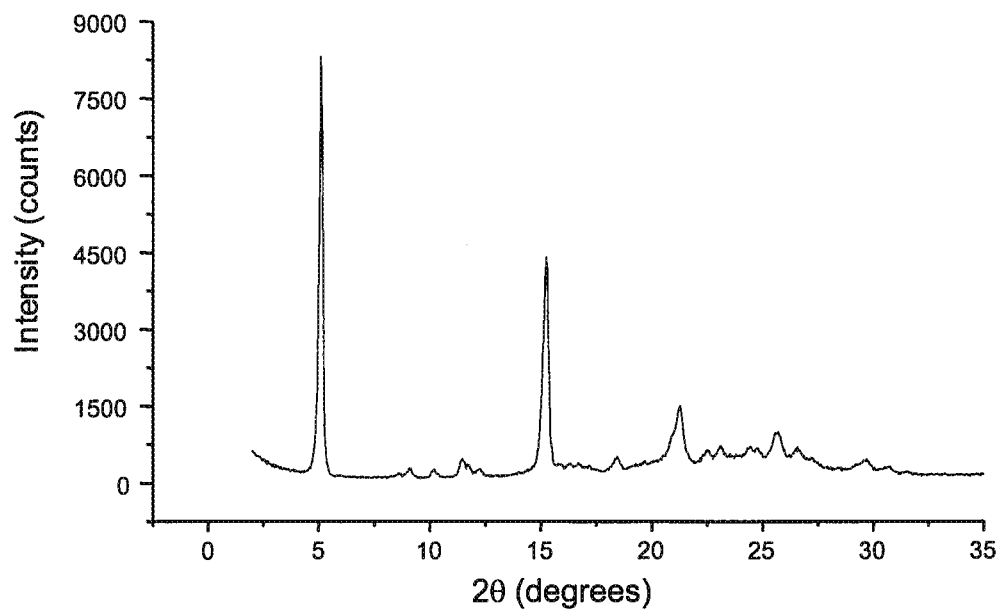
FIGS. 3 and 4 show powder x-ray diffraction (PXRD) patterns of samples of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention.
Figure 4:
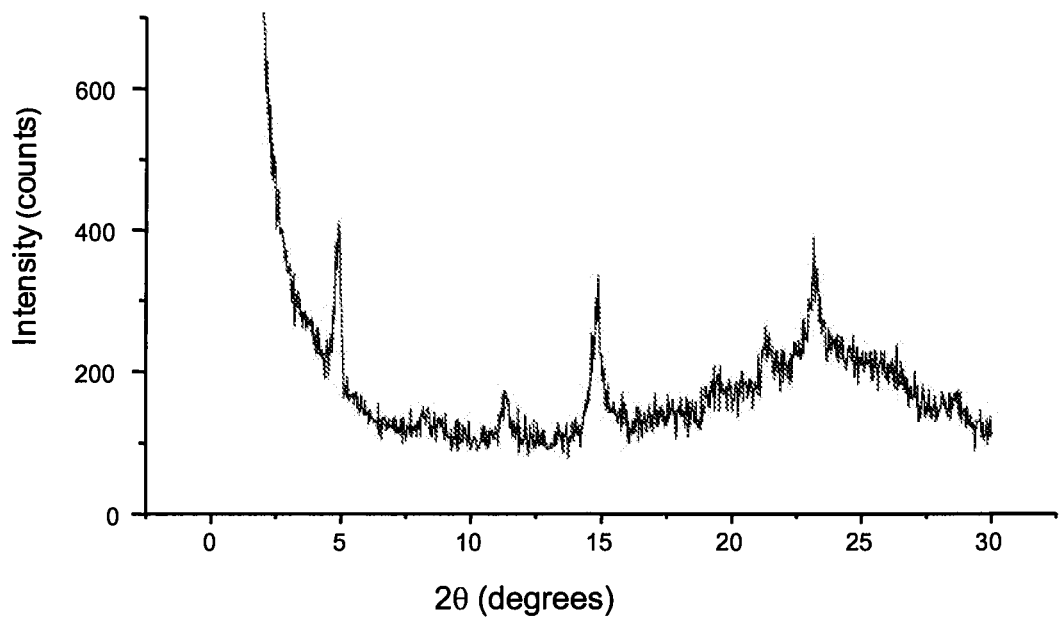

In another embodiment, the crystalline 1,2-ethanedisulfonic acid salt of the present invention is characterized by a powder x-ray diffraction (PXRD) pattern having significant diffraction peaks at 2θ values of 5.0±0.3, and 15.0±0.3. Subtle differences may be observed between the peak positions in the PXRD spectrum of a crystalline salt prepared by recrystallization from a high melting point seed crystal, as shown in FIG. 3 and that of a salt prepared without use of such a seed crystal, as shown in FIG. 4. Accordingly in separate embodiments, the crystalline 1,2-ethanedisulfonic acid salt of the compound of formula I is characterized by a powder x-ray diffraction pattern in which the peak positions are substantially in accordance with those shown in FIG. 3 or with those shown in FIG. 4.

Figure 5:
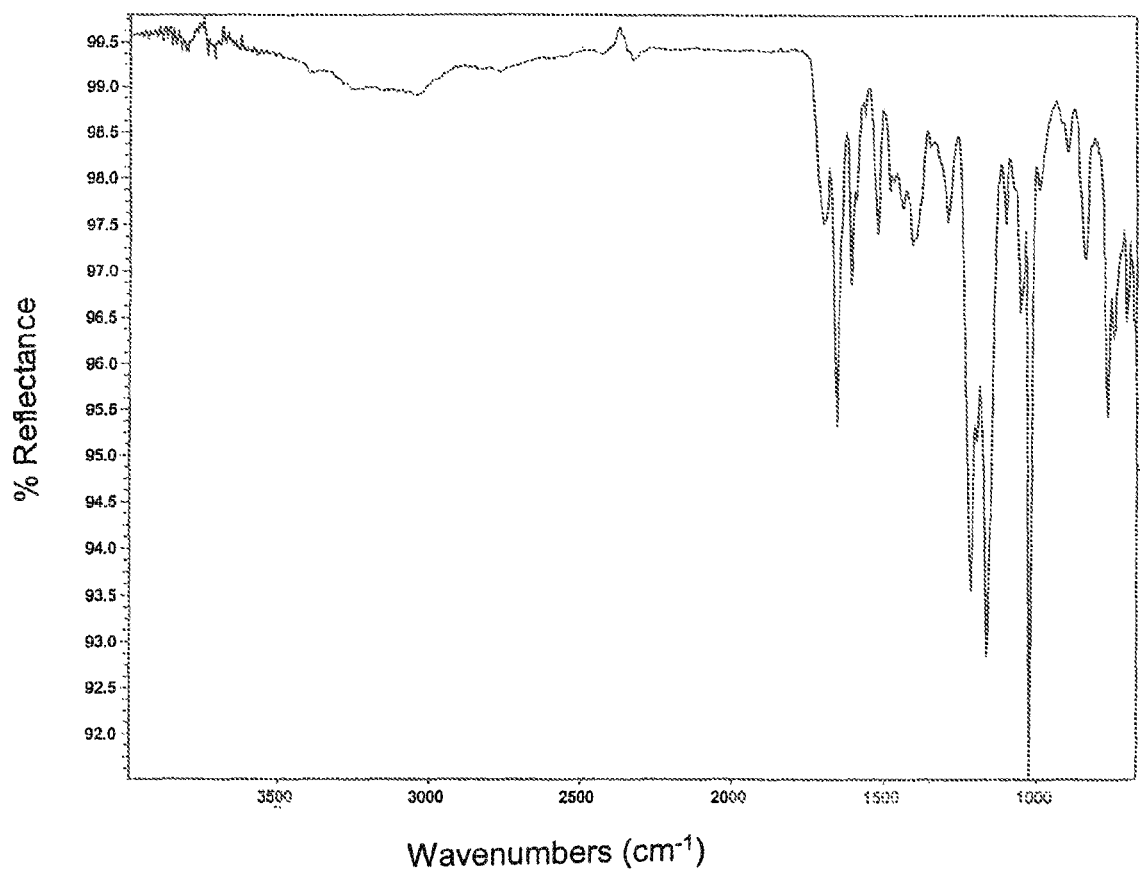
FIG. 5 shows an infrared (IR) absorption spectra for a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention.

In another embodiment, the crystalline 1,2-ethanedisulfonic acid salt of the compound of formula I is characterized by its infrared (IR) absorption spectrum which shows significant absorption bands at about 704, 748, 768, 841, 900, 1055, 1104, 1166, 1218, 1294, 1408, 1522, 1609, 1655, and 1701 cm$^{-1}$, as illustrated in FIG. 5.

A crystalline 1,2-ethanedisulfonic acid salt of the compound of formula I has been demonstrated to have a reversible sorption/desorption profile with an acceptable, moderate level of hygroscopicity (i.e., less than about 2.5% weight gain in the humidity range of 40% relative humidity to 75% relative humidity).

These properties of the salts of this invention are further illustrated in the Examples below.

Pharmaceutical Compositions and Formulations

The 1,2-ethanedisulfonic acid salt of the compound of formula I is typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. However, it will be understood by those skilled in the art that, once the crystalline salt of this invention has been formulated, it may no longer be in crystalline form, i.e., the salt may be dissolved in a suitable carrier.

Accordingly, in one of its compositions aspects, this invention is directed to a pharmaceutical composition comprising a pharmaceutically acceptable carrier or excipient and a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. Optionally, such pharmaceutical compositions may contain other therapeutic and/or formulating agents if desired.

The pharmaceutical compositions of this invention typically contain a therapeutically effective amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. Typically, such pharmaceutical compositions will contain from about 0.01 to about 95% by weight of the active agent;

including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or exipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a salt of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patients respiratory tract. Accordingly, when formulated for use in a nebulizer inhaler, the active agent is typically dissolved in a suitable carrier to form a solution. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 and WO 97/12687.

A representative pharmaceutical composition for use in a nebulizer inhaler comprises an aqueous solution comprising from about 0.05 µg/mL to about 10 mg/mL of a 1,2-ethanedisulfonic acid salt of compound of formula I or a solvate thereof. In one embodiment, the aqueous nebulizer formulation is isotonic. In one embodiment, the aqueous nebulizer formulation has a pH in the range of from about 4 to about 6. In a particular embodiment, the aqueous nebulizer formulation is buffered with citrate buffer to a pH of about 5. In another particular embodiment, the aqueous nebulizer formulation contains from about 0.1 mg/mL to about 1.0 mg/mL free base equivalents of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester.

In another specific embodiment of this invention, the pharmaceutical composition comprising the active agent is administered by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose, starch, mannitol, dextrose, polylactic acid (PLA), polylactide-co-glycolide (PLGA) or combinations thereof. Typically, the active agent is micronized and combined with a suitable carrier to form a blend of micronized particles of respirable size, where "micronized particles" or "micronized form" means at least about 90% of the particles have a diameter of less than about 10 µm.

A representative pharmaceutical composition for use in a dry powder inhaler comprises lactose having a particle size between about 1 µm and about 100 µm and micronized particles of a 1,2-ethanedisulfonic acid salt of compound of formula I, or a solvate thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); Rotahaler GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as CCl$_3$F, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183, EP 0717987 A2, and WO 92/22286.

A representative pharmaceutical composition for use in a metered-dose inhaler comprises from about 0.01% to about 5% by weight of a 1,2-ethanedisulfonic acid salt of compound of formula I, or a solvate thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. Nos. 6,006,745 and 6,143,277. Alternatively, a suspension formulation can be prepared by spray drying a coating of surfactant on micronized particles of the active agent. See, for example, WO 99/53901 and WO 00/61108.

For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a salt of the present invention as an active ingredient.

When intended for oral administration in a solid dosage form (i.e., as capsules, tablets, pills and the like), the pharmaceutical compositions of this invention will typically comprise a salt of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid!methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, such has polylactic acid (PLA) or polylactide-co-glycolide (PLGA), liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

When intended for oral administration, the pharmaceutical compositions of this invention are preferably packaged in a unit dosage form. For example, such unit dosage forms may be capsules, tablets, pills, and the like.

The salts of this invention can also be administered transdermally using known transdermal delivery systems and excipients. For example, a compound of this invention can be admixed with permeation enhancers, such as propylene glycol, polyethylene glycolm monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a 1,2-ethanedisulfonic acid salt of compound of formula I or solvate thereof. For example, the pharmaceutical compositions of this invention may further comprise one or more therapeutic agents selected from anti-inflammatory agents (e.g. steroidal anti-inflammatory agents, such as corticosteroids; and non-steroidal anti-inflammatory agents (NSAIDs), phosphodiesterase IV inhibitors, antiinfective agents (e.g. antibiotics or antivirals), antihistamines, $\beta_2$ adrenergic receptor agonists, muscarinic receptor antagonist (i.e., anticholinergic agents) and the like. The other therapeutic agents can be used in the form of pharmaceutically acceptable salts or solvates. Additionally, if appropriate, the other therapeutic agents can be used as optically pure stereoisomers.

If desired, the salts of this invention can also be administered in combination with another therapeutic agent or agents, such those described herein. In this embodiment, the components are not physically mixed together hut are administered simultaneously or sequentially as separate compositions. For example, a salt of this invention can be administered by inhalation simultaneously or sequentially with a steroidal anti-inflammatory agent, such as a corticosteroid, using an inhalation delivery device that employs separate compartments (e.g. blister packs) for each therapeutic agent. Alternatively, the combination may be administered from multiple delivery devices, i.e., one delivery device for each therapeutic agent.

Representative $\beta_2$ adrenergic receptor agonists that can be used in combination with the compounds of this invention include, but are not limited to, salmeterol, salbutamol, formoterol, salmefamol, fenoterol, terbutaline, albuterol, isoetharine, metaproterenol, pirbuterol, levalbuterol and the like, or pharmaceutically acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}amino)heptyl]oxy}propyl)benzenesulfonamide and related compounds disclosed in WO 02/066422, published on Aug. 29, 2002; 3-[3-(4-{[6-({(2R)-2-hydroxy-2-[4-hydroxy-3-(hydroxymethyl)phenyl]ethyl}amino)hexyl]-oxy}butyl)phenyl]imidazolidine-2,4-dione and related compounds disclosed in WO 02/070490, published Sep. 12, 2002; 3-(4-{[6-({(2R)-2-[3-(formylamino)-4-hydroxyphenyl]-2-hydroxyethyl}amino)hexyl]oxy}butyl)benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}benzenesulfonamide, N-(tert-butyl)-3-(4-{[6-({(2R)-2-[3-(formylamino)-4-hydroxyphenyl]-2-hydroxyethyl}amino)hexyl]-oxy}butyl)benzenesulfonamide, N-(tert-butyl)-3-(4-{[6-({(2S)-2-[3-(formylamino)-4-hydroxyphenyl]-2-hydroxyethyl}amino)hexyl]oxy}butyl)benzenesulfonamide, N-(tert-butyl)-3-(4-{[6-({(2R/S)-2-[3-(formylamino)-4-hydroxyphenyl]-2-hydroxyethyl}amino)hexyl]oxy}butyl)benzenesulfonamide and related compounds disclosed in WO 02/076933, published on Oct. 3, 2002; 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439, published on Mar. 27, 2003; N-{2-[4-((R)-2-hydroxy-2-phenylethylamino)phenyl]ethyl}-(R)-2-hydroxy-2-(3-formamido-4-hydroxyphenyl)ethylamine and related compounds disclosed in U.S. Pat. No. 6,576,793 B1, issued on Jun. 10, 2003; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 B2, issued on Nov. 25, 2003; and pharmaceutically acceptable salts thereof. In a particular embodiment, the $\beta_2$-adrenoreceptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 µg to about 500 µg per dose.

Representative steroidal anti-inflammatory agents that can be used in combination with the compounds of this invention include, but are not limited to, methyl prednisolone, prednisolone, dexamethasone, fluticasone propionate, 6,9-difluoro-17-[(2-furanylcarbonyl)oxy]-11-hydroxy-16-methyl-3-oxoandrosta-1,4-diene-17-carbothioic acid S-fluoromethyl ester, 6,9-difluoro-11-hydroxy-16-methyl-3-oxo-17-propionyloxy-androsta-1,4-diene-17-carbothioic acid S-(2-oxotetrahydrofuran-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-acceptable salts thereof. In a particular embodiment, the steroidal anti-inflammatory agent is 6α,9α-difluoro-17α-[(2-furanylcarbonyl)oxy]-11β-hydroxy-16α-methyl-3-oxoandrosta-1,4-diene-17β-carbothioic acid S-fluoromethyl ester or a pharmaceutically acceptable salt or solvate thereof. When employed, the steroidal anti-inflammatory agent will be present in the pharmaceutical composition in a therapeutically effective amount. Typically, the steroidal anti-inflammatory agent will be present in an amount sufficient to provide from about 0.05 µg to about 500 µg per dose.

Other suitable combinations include, for example, other anti-inflammatory agents, e.g., NSAIDs (such as sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (IL antibody), specifically, an IL-4 therapy, an IL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesarma); VM554/UM565 (Vernalis); T-440 (Tanabe Seiyaku); and T2585 (Tanabe Seiyaku).

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d,l) hydrobromide, scopolamine hydrobromide, ipratropium bromide, oxitropium bromide, tiotropium bromide, methanthetine, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Suitable doses for the other therapeutic agents administered in combination with a compound of the invention are in the range of about 0.05 mg/day to about 100 mg/day.

The following formulations illustrate representative pharmaceutical compositions of the present invention:

Formulation Example A

A dry powder for administration by inhalation is prepared as follows:

| Ingredients | Amount |
|---|---|
| Salt of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

Formulation Example B

A dry powder formulation for use in a dry powder inhalation device is prepared as follows:
Representative Procedure: A pharmaceutical composition is prepared having a hulk formulation ratio of micronized salt of the invention to lactose of 1:200. The composition is packed into a powder inhalation device capable of delivering between about 10 μg and about 100 μg of the compound of the invention per dose.

Formulation Example C

A dry powder for administration by inhalation in a metered dose inhaler is prepared as follows:
Representative Procedure: A suspension containing 5 wt. % of a salt of the invention and 0.1 wt. % lecithin is prepared by dispersing 10 g of the compound of the invention as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example D

A pharmaceutical composition for use in a metered dose inhaler is prepared as follows:
Representative Procedure: A suspension containing 5% salt of the invention, 0.5% lecithin, and 0.5% trehalose is prepared by dispersing 5 g of active ingredient as micronized particles with mean size less than 10 m in a colloidal solution formed from 0.5 g of trehalose and 0.5 g of lecithin dissolved in 100 mL demineralized water. The suspension is spray dried and the resulting material is micronized to particles having a mean diameter less than 1.5 μm. The particles are loaded into canisters with pressurized 1,1,1,2-tetrafluoroethane.

Formulation Example E

A pharmaceutical composition for use in a nebulizer inhaler is prepared as follows:
Representative Procedure: An aqueous aerosol formulation for use in a nebulizer is prepared by dissolving 0.5 mg of the salt of the invention in 1 mL of a 0.9% sodium chloride solution acidified with citric acid. The mixture is stirred and sonicated until the active ingredient is dissolved. The pH of the solution is adjusted to a value of about 5 by the slow addition of NaOH.

Formulation Example F

Hard gelatin capsules for oral administration are prepared as follows:

| Ingredients | Amount |
|---|---|
| Salt of the invention | 250 mg |
| Lactose (spray-dried) | 200 mg |
| Magnesium stearate | 10 mg |

Representative Procedure: The ingredients are thoroughly blended and then loaded into a hard gelatine capsule (460 mg of composition per capsule).

Formulation Example G

A suspension for oral administration is prepared as follows:

| Ingredients | Amount |
|---|---|
| Salt of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

Formulation Example H

An injectable formulation is prepared as follows:

| Ingredients | Amount |
| --- | --- |
| Salt of the invention | 0.2 g |
| Sodium acetate buffer solution (0.4M) | 2.0 mL |
| HCl (0.5N) or NaOH (0.5N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Utility

The compound of formula I possesses both $\beta_2$ adrenergic receptor agonist and muscarinic receptor antagonist activity and therefore, a 1,2-ethanedisulfonic acid salt of the compound of formula I of the present invention is expected to be useful as a therapeutic agent for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other conditions which may be treated include premature labor, depression, congestive heart failure, skin diseases (e.g., inflammatory, allergic, psoriatic and proliferative skin diseases, conditions where lowering peptic acidity is desirable (e.g., peptic and gastric ulceration) and muscle wasting disease.

Accordingly, in one embodiment, this invention is directed to a method for treating a pulmonary disorder, the method comprising administering to a patient in need of treatment a therapeutically effective amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. When used to treat a pulmonary disorder, the salt of this invention will typically be administered by inhalation in multiple doses per day, in a single daily dose or a single weekly dose. Generally, the dose for treating a pulmonary disorder will range from about 10 μg/day to about 200 μg/day.

When administered by inhalation, the compounds of this invention typically have the effect of providing bronchodilation. Accordingly, in another of its method aspects, this invention is directed to a method of providing bronchodilation in a patient in need of bronchodilation, the method comprising administering to the patient a bronchodilation-producing amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. Generally, the dose for providing bronchodilation will range from about 10 μg/day to about 200 μg/day.

In one embodiment, this invention is directed to a method of treating chronic obstructive pulmonary disease or asthma, the method comprising administering to a patient in need of treatment a therapeutically effective amount of a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]-piperidin-4-yl ester or a solvate thereof. When used to treat a COPD or asthma, the salt of this invention will typically be administered by inhalation multiple doses per day or in a single daily dose. Generally, the dose for treating COPD or asthma will range from about 10 μg/day to about 200 μg/day. As used herein, COPD includes chronic obstructive bronchitis and emphysema (see, for example, Barnes, Chronic Obstructive Pulmonary Disease, *N Engl J Med* 2000: 343:269-78).

When used to treat a pulmonary disorder, the salt of this invention is optionally administered in combination with other therapeutic agents. Accordingly, in a particular embodiment, the pharmaceutical compositions and methods of this invention further comprise a therapeutically effective amount of a steroidal anti-inflammatory agent. The properties and utility of 1,2-ethanedisulfonic acid salts of this invention can be demonstrated using various in vitro and in vivo assays well-known to those skilled in the art. For example, representative assays are described in further detail in the following Examples.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard meaning:

AC adenylyl cyclase
Ach acetylcholine
ATCC American Type Culture Collection
BSA bovine serum albumin
cAMP cyclic adenosine monophosphate
CHO Chinese hamster ovary
$cM_5$ cloned chimpanzee $M_5$ receptor
DCM dichloromethane (i.e., methylene chloride)
DIPEA N,N-diisopropylethylamine
dPBS Dulbecco's phosphate buffered saline
DMEM Dulbecco's Modified Eagle's Medium
DMSO dimethyl sulfoxide
EDTA ethylenediaminetetraacetic acid
Emax maximal efficacy
EtOAc ethyl acetate
EtOH ethanol
FBS fetal bovine serum
FLIPR fluorometric imaging plate reader
Gly glycine
HATU O-(7-azabenzotriazol-1-yl-N,N,N',N'-tetramethyluronium hexafluorophosphate
HBSS Hank's buffered salt solution
HEK human embryonic kidney cells
HEPES 4-(2-hydroxyethyl)-1-piperazineethanesulfonic acid
$hM_1$ cloned human $M_1$ receptor
$hM_2$ cloned human $M_2$ receptor
$hM_3$ cloned human $M_3$ receptor
$hM_4$ cloned human $M_4$ receptor
$hM_5$ cloned human $M_5$ receptor
HPLC high-performance liquid chromatography
IBMX 3-isobutyl-1-methylxanthine
% Eff % efficacy
PBS phosphate buffered saline PyBOP benzotriazol-1-yloxytripyrrolidinophosphonium hexafluorophosphate
rpm rotations per minute
TFA trifluoroacetic acid
THF tetrahydrofuran
Tris tris(hydroxymethyl)aminomethane Unless noted otherwise, reagents, starting materials and solvents were purchased from commercial suppliers (such as Aldrich, Fluka, Sigma and the like) and were used without further purification.

In the examples described below, HPLC analysis was conducted using an Agilent (Palo Alto, Calif.) Series 1100 instrument with Zorbax Bonus RP 2.1×50 mm columns, supplied by Agilent, (a C14 column), having a 3.5 micron particle size. Detection was by UV absorbance at 214 nm. HPLC 10-70 data was obtained with a flow rate of 0.5 mL/minute of 10%-70% B over 6 minutes, Mobile phase A was 2%-98%-0.1% ACN-H$_2$O-TFA; and mobile phase B was 90%-10%-0.1% ACN-H$_2$O-TFA. Using the mobile phases A and B described above, HPLC 5-35 data and HPLC 10-90 data were obtained with a 5 minute gradient.

Liquid chromatography mass spectrometry (LCMS) data were obtained with an Applied Biosystems (Foster City, Calif.) model API-150EX instrument. LCMS 10-90 data was obtained with a 10%-90% mobile phase B over a 5 minute gradient.

Small scale purification was conducted using an API 150EX Prep Workstation system from Applied Biosystems. The mobile phase was A: water+0.05% v/v TFA; and B: acetonitrile+0.05% v/v TFA. For arrays (typically about 3 to 50 mg recovered sample size) the following conditions were used: 20 mL/min flow rate; 15 min gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 min gradients and a 41.4 mm×250 mm Microsorb BDS column with 10 micron particles (Varian, Palo Alto, Calif.).

The specific rotation for chiral compounds (indicated as $[\alpha]^{20}_D$) was measured using a Jasco Polarimeter (Model P-1010) with a tungsten halogen light source and a 589 nm filter at 20° C. Samples of test compounds were typically measured at 1 mg/mL water.

Preparation 1

Methyl 4-Amino-5-chloro-2-methoxybenzoate

To a solution of 4-amino-5-chloro-2-methoxybenzoic acid (1.008 g, 5.0 mmol) in a mixture of toluene (9 mL) and methanol (1 mL) at 0° C. was added (trimethylsilyl)diazomethane (2.0 M in hexane, 3.0 mL, 6.0 mmol) dropwise. The reaction mixture was then warmed to room temperature and stirred for 16 h. Excess (trimethylsilyl)diazomethane was quenched by adding acetic acid until the bright yellow color of the reaction mixture disappeared. The mixture was then concentrated in vacuo to give the title compound as an off-white solid, which was used without further purification.

Preparation 2

Methyl 4-Acryloylamino-5-chloro-2-methoxybenzoate

To crude product of Preparation 2 was added dichloromethane (10 mL, 0.5 M) and triethylamine (2.1 mL, 15 mmol). This mixture was cooled to 0° C. and acryloyl chloride (812 μL, 10 mmol) was added dropwise with stirring. After 2 h, the reaction was quenched by adding methanol (about 2 mL) at 0° C. and the resulting mixture was stirred at room temperature for 15 min and then concentrated in vacuo. Dichloromethane (30 mL) and water (30 mL) were added to the residue and this mixture was mixed thoroughly. The layers were separated and the aqueous layer was extracted with dichloromethane (20 mL). The organic layers were combined, dried (Na$_2$SO$_4$), filtered and the solvent was removed in vacuo to give the title compound as a brown foamy solid, which was used without further purification.

Preparation 3

Biphenyl-2-ylcarbamic Acid Piperidin-4-yl Ester

Biphenyl-2-isocyanate (97.5 g, 521 mmol) and 4-hydroxy-1-benzylpiperidine (105 g, 549 mmol), both commercially-available from Aldrich, Milwaukee, Wis., were heated together at 70° C. for 12 h, during which time the formation of biphenyl-2-ylcarbamic acid 1-benzylpiperidin-4-yl ester was monitored by LCMS. The reaction mixture was then cooled to 50° C. and ethanol (1 L) was added, and then 6M hydrochloric acid (191 mL) was added slowly. The reaction mixture was then cooled to ambient temperature and ammonium formate (98.5 g, 1.56 mol) was added and nitrogen gas was bubbled through the solution vigorously for 20 min. Palladium (10 wt. % (dry basis) on activated carbon) (20 g) was then added. The reaction mixture was heated at 40° C. for 12 h and then filtered through a pad of Celite. The solvent was then removed under reduced pressure and 1M hydrochloric acid (40 mL) was added to the crude residue. Sodium hydroxide (10N) was then added to adjust the pH to 12. The aqueous layer was extracted with ethyl acetate (2×150 mL) and dried (magnesium sulfate), and then the solvent was removed under reduced pressure to give the title compound (155 g, 100%). HPLC (10-70) $R_f$=2.52; MS m/z: [M+H$^+$] calc'd for $C_{18}H_{20}N_2O_2$ 297.15. found 297.3.

Preparation 4

Methyl 4-{3-[4-(Biphenyl-2-ylcarbamoyloxy)piperidin-1-yl]propionylamino}-5-chloro-2-methoxybenzoate To the crude product from Preparation 2 was added the product of Preparation 3 (1.33 g, 4.5 mmol) and a mixture of THF (22.5 mL) and methanol (2.5 mL). This mixture was heated at 50° C. with stirring for 16 h and then the solvent was removed in vacuo. The residue was chromatographed (silica gel; EtOAc) to give the title compound (0.82 g; $R_f$=0.4, 29% yield over 3 steps) as an off-white foamy solid. MS m/z 566.4 (M+H, expected 565.20 for $C_{30}H_{32}ClN_3O_6$).

Preparation 5

Biphenyl-2-ylcarbamic Acid 1-[2-(2-Chloro-4-hydroxymethyl-5-methoxy-phenylcarbamoyl)ethyl] piperidin-4-yl Ester To a solution of the product of Preparation 4 (0.82 mg, 1.45 mmol) in a mixture of THF (4.5 mL) and methanol (0.5 mL) at 0° C. was added lithium borohydride (32 mg, 1.45 mmol). The reaction mixture was allowed to warm to room temperature and was stirred for 41 h. The reaction was then quenched by adding 1N aqueous hydrochloric acid at 0° C. until no more bubbling was observed and this mixture was stirred for 10 min. The solvent was removed in vacuo and the residue was dissolved in acetonitrile (about 2 mL). This solution was purified by prep-RP-HPLC (gradient: 2 to 50% acetonitrile in water with 0.05% TFA). The appropriate fractions were collected and combined and lyophilized to give the title compound as a trifluoroacetate salt. This salt was treated with isopropyl acetate (10 mL) and 1N aqueous sodium hydroxide (10 mL) and the organic layer was collected, dried ($Na_2SO_4$), filtered and the solvent was removed in vacuo to give the title compound (161 mg, 21% yield) as a white foamy solid. MS m/z 538.4 (M+H, expected 537.20 for $C_{29}H_{32}ClN_3O_5$).

Preparation 6

Biphenyl-2-ylcarbamic Acid 1-[2-(2-Chloro-4-formyl-5-methoxyphenyl-carbamoyl)ethyl]piperidin-4-yl Ester To a solution of the product of Preparation 5 (161 mg, 0.3 mmol) in dichloromethane (3 mL) was added dimethyl sulfoxide (213 µL, 3.0 mmol) and diisopropylethylamine (261 µL, 1.5 mmol). This mixture was cooled to −20° C. and sulfur trioxide pyridine complex (238 mg, 1.5 mmol) was added slowly. After 30 min, the reaction mixture was quenched by adding water (about 3 mL). The layers were separated and the organic layer was dried ($Na_2SO_4$), filtered and the solvent was removed in vacuo to give the title compound as a light yellow solid. MS m/z 536.3 (M+H, expected 535.19 for $C_{29}H_{30}ClN_3O_5$).

Preparation 7

8-Benzyloxy-5-(2-bromoacetyl)-1H-quinolin-2-one (a) 8-Acetoxy-1H-quinolin-2-one

8-Hydroxyquinoline-N-oxide (160.0 g, 1.0 mol), commercially-available from Aldrich, Milwaukee, Wis., and acetic anhydride (800 mL, 8.4 mol) were heated at 100° C. for 3 h and then cooled in ice. The product was collected on a Buchner funnel, washed with acetic anhydride (2×100 mL) and dried under reduced pressure to give 8-acetoxy-1H-quinolin-2-one (144 g) as a solid.

(b) 5-Acetyl-8-hydroxy-1H-quinolin-2-one

A slurry of aluminum chloride (85.7 g, 640 mmol) in 1,2-dichloroethane (280 mL) was cooled in ice, and the product from step (a) (56.8 g, 280 mmol) was added. The mixture was warmed to room temperature and then heated at 85° C. After 30 min, acetyl chloride (1.5 mL, 21 mmol) was added and the mixture was heated an additional 60 min. The reaction mixture was then cooled and added to 1N hydrochloric acid (3 L) at 0° C. with good stirring. After stirring for 2 h, the solids were collected on a Buchner funnel, washed with water (3×250 mL) and dried under reduced pressure. The crude product isolated from several batches (135 g) was combined and triturated with dichloromethane (4 L) for 6 h. The resulting solid was collected on a Buchner funnel and dried under reduced pressure to give the title compound (121 g).

(e) 5-Acetyl-8-benzyloxy-1H-quinolin-2-one

To the product from step (b) (37.7 g, 186 mmol) was added N,N-dimethylformamide (200 mL) and potassium carbonate (34.5 g, 250 mmol) followed by benzyl bromide (31.8 g, 186 mmol). The mixture was stirred at room temperature for 2.25 hour and then poured into saturated sodium chloride (3.5 L) at 0° C. and stirred for 1 hour. The product was collected and dried on a Buchner funnel for 1 hour, and the resulting solids were dissolved in dichloromethane (2 L) and this mixture was dried over sodium sulfate. The solution was filtered through a pad of Celite which was then washed with dichloromethane (5×200 mL). The combined filtrate was then concentrated to dryness and the resulting solids were triturated with ether (500 mL) for 2 h. The product was collected on a Buchner funnel, washed with ether (2×250 mL) and dried under reduced pressure to give the title compound (44 g) as a powder.

(d) 8-Benzyloxy-5-(2-bromoacetyl)-1H-quinolin-2-one

The product from step (c) (20.0 g, 68.2 mmol) was dissolved in dichloromethane (200 mL) and cooled to 0° C. Boron trifluoride diethyl etherate (10.4 mL, 82.0 mmol) was added via syringe and the mixture was warmed to room temperature to give a thick suspension. The suspension was heated at 45° C. (oil bath) and a solution of bromine (11.5 g, 72.0 mmol) in dichloromethane (100 mL) was added over 40 min. The mixture was kept at 45° C. for an additional 15 min and then cooled to room temperature. The mixture was concentrated under reduced pressure and then triturated with 10% aqueous sodium carbonate (200 mL) for 1 hour. The solids were collected on a Buchner funnel, washed with water (4×100 mL) and dried under reduced pressure. The product of two runs was combined for purification. The crude product (52 g) was triturated with 50% methanol in chloroform (500 mL) for 1 hour. The product was collected on a Buchner funnel and washed with 50% methanol in chloroform (2×50 mL) and methanol (2×50 mL). The solid was dried under reduced pressure to give the title compound (34.1 g) as a powder.

Preparation 8

8-Benzyloxy-5-[(R)-2-bromo-1-(tert-butyldimethyl-silanyloxy)ethyl]-1H-quinolin-2-one (a) 8-Benzyloxy-5-((R)-2-bromo-1-hydroxyethyl)-1H-quinolin-2-one (R)-(+)-α,α-Diphenylprolinol (30.0 g, 117 mmol) and trimethylboroxine (11.1 mL, 78 mmol) were combined in toluene (300 mL) and stirred at room temperature for 30 min. The mixture was placed in a 150° C. oil bath and liquid was distilled off. Toluene was added in 20 mL aliquots and distillation was continued for 4 h. A total of 300 mL toluene was added. The mixture was then cooled to room temperature. A 500 µL aliquot was evaporated to dryness and weighed (246 mg) to determine that the concentration of catalyst was 1.8 M.

8-Benzyloxy 5-(2-bromoacetyl)-1H-quinolin-2-one (90.0 g, 243 mmol) was placed under nitrogen and tetrahydrofuran (900 mL) was added followed by the catalyst described above (1.8 M in toluene, 15 mL, 27 mmol). The suspension was cooled to −10±5° C. in an ice/isopropanol bath. Borane (1.0 M in THF, 294 mL, 294 mmol) was added over 4 h. The reaction was then stirred an additional 45 min at −10° C. and then methanol (250 mL) was added slowly. The mixture was concentrated under vacuum and the residue was dissolved in boiling acetonitrile (1.3 L), filtered while hot and then cooled to room temperature. The crystals were filtered, washed with acetonitrile and dried under vacuum to give the title compound (72.5 g, 196 mmol, 81% yield, 95% ee, 95% pure by HPLC).

(b) 8-Benzyloxy-5-[(R)-2-bromo-1-(tert-butyldimethylsilanyloxy)ethyl]-1H-quinolin-2-one To the product of step (b) (70.2 g, 189 mmol) was added N,N-dimethylformamide (260 mL) and this mixture was cooled in an ice bath under nitrogen, 2,6-Lutidine (40.3 g, 376 mmol) was added over 5 min and then tert-butyldimethylsilyl trifluoromethanesulfonate (99.8 g, 378 mmol) was added slowly while maintaining the temperature below 20° C. The mixture was allowed to warm to room temperature for 45 min. Methanol (45 mL) was added to the mixture dropwise over 10 min and the mixture was partitioned between ethyl acetate/cyclohexane (1:1, 500 mL) and water/brine (1:1, 500 mL). The organics were washed twice more with water/brine (1:1, 500 mL each). The combined organics were evaporated under reduced pressure to give a light yellow oil. Two separate portions of cyclohexane (400 mL) were added to the oil and distillation continued until a thick white slurry was formed. Cyclohexane (300 mL) was added to the slurry and the resulting white crystals were filtered, washed with cyclohexane (300 mL) and dried under reduced pressure to give the title compound (75.4 g, 151 mmol, 80% yield, 98.6% ee).

Preparation 9A

8-Benzyloxy-5-[(R)-2-(N-benzylamino)-1-(tert-butyldimethylsilanyloxy)ethyl]-1H-quinolin-2-one A stirred solution of the product of Preparation 8 (1.00 g, 2.05 mmol) and benzylamine (493 µL, 4.51 mmol) in DMSO (1.7 mL) was heated at 105° C. for 4 h. The reaction mixture was allowed to cool and was then diluted with EtOAc (10 mL) and the organic layer was washed with saturated aqueous ammonium chloride solution (5 mL) and 1N sodium hydroxide (5 mL), dried (MgSO$_4$) and solvent removed under reduced pressure. The crude residue was purified by column chromatography (50% EtOAc/hexanes) to give the title compound (700 mg, 67%). MS m/z: [M+H$^+$] calcd for C$_{31}$H$_{38}$N$_2$O$_3$Si 515.27. found 515.5.

Preparation 9B

8-Benzyloxy-5-[(R)-2-(N-benzylamino)-1-(tert-butyldimethylsilanyloxy)ethyl]-1H-quinolin-2-one To a 500 mL three-necked round-bottom flask was added 8-benzyloxy-5-[(R)-2-bromo-1-(tert-butyldimethylsilanyloxy)ethyl]-1H-quinolin-2-one (43 g, 0.124 mol, about 95% chiral purity), 1-methyl-2-pyrrolidinone (210 mL) and benzylamine (28.3 g, 0.37 mol). The resulting mixture was flushed with nitrogen and then stirred at 90° C. for 6 hours. The mixture was then cooled to room temperature and water (300 mL) and ethyl acetate (300 mL) were added. The layers were separated and the organic layer was washed with water (200 mL), a 1:1 mixture of water and aqueous saturated sodium chloride solution (200 mL), and water (200 mL). The organic layer was then dried over magnesium sulfate, filtered and concentrated under reduced pressure to provide the title compound as an orange oil.

To the orange oil was added heptane (200 mL) and ethyl acetate (200 mL) and the resulting mixture was heated to 65° C. to produce a clear solution. This solution was cooled to room temperature and allowed to stand overnight (about 16 hours) at which time a precipitate had formed. The precipitate was collected by filtration to give stereochemically-impure title compound (8.85 g, 79.6% ee). The filtrate was concentrated under reduced pressure to give the title compound (38.6 g, 99.4% ee). This material was combined with a previous batch of material (19.2 g, 99.5% ee) and heptane (250 mL) and ethyl acetate (100 mL) were added. This mixture was heated to 80° C. (hazy to clear solution) and then cooled to room temperature and allowed to stand overnight. The resulting precipitate was collected by filtration to afford the title compound as a white solid (36.8 g. 98.4% ee, 99.9% chemical purity). The filtrate was concentrated under reduced pressure and the residue was dissolved in heptane (100 mL). The resulting solids were collected to give the title compound as a tan solid (24 g, 100% chiral purity, 95% chemical purity).

Preparation 10A

5-[(R)-2-Amino-1-(tert-butyldimethylsilanyloxy)ethyl]-8-hydroxy-1H-quinolin-2-one A stirred solution of the product of Preparation 9A (3.16 g, 6.15 mmol) and palladium (10 wt. % (dry basis) on activated carbon) (1.58 g) in ethanol (62 mL) was placed under an atmosphere of hydrogen for 24 h. The reaction mixture was filtered through Celite, washed with methanol (15 mL), and then the solvent was removed under reduced pressure to give the title compound as a solid (1.52 g, 4.55 mmol, 74%).

Preparation 10B

5-[(R)-2-Amino-1-(tert-butyldimethylsilanyloxy)ethyl]-8-hydroxy-1H-quinolin-2-one Acetic Acid Salt 8-Benzyloxy-5-[(R)-2-(N-benzylamino)-1-(tert-butyldimethylsilanyloxy)ethyl]-1H-quinolin-2-one (100 g, 194 mmol) and acetic acid (17.5 mL, 291 mmol) were dissolved in methanol (1 L). The clear solution was purged with nitrogen and then palladium hydroxide on carbon (20 g, 20 wt. % Pd (dry basis), wet (about 50% water)) was added. Hydrogen gas was bubbled through the stirred solution at room temperature for 6 hours during which time a thick slurry developed. The reaction mixture was then purged with nitrogen and methanol (1 L) was added. The resulting mixture was stirred for about 30 minutes (to dissolve the product) and then the mixture was filtered through a pad of Celite. The filterate was concentrated under reduced pressure to a volume of about 500 mL and, to the resulting slurry, was added ethanol (500 mL). The resulting mixture was again concentrated under reduced pressure to a volume of about 500 mL and the resulting precipitate was collected by filtration and dried to provide the title compound as a yellow-white solid (65 g, 85% yield, >98% purity).

Preparation 11

Biphenyl-2-ylcarbamic Acid 1-[2-(4-{[(R)-2-(tert-Butyldimethylsilanyloxy)-2-(8-hydroxy-2-oxo-1,2-dihydroquinolin-5-yl)ethylamino]methyl}-2-chloro-5-methoxy-phenylcarbamoyl)ethyl]piperidin-4-yl Ester To the product from Preparation 6 in a mixture of dichloromethane (0.5 mL) and methanol (0.5 mL) was added the product of Preparation 10A (124.1 mg, 3.1 mmol) and the resulting mixture was stirred at room temperature for 1.5 h. Sodium triacetoxyborohydride (190.7 mg, 0.9 mmol) was added and the resulting mixture was stirred at room temperature for 15 h. The reaction was quenched by adding water (about 0.2 mL) and the mixture was concentrated in vacuo to give the title compound, which was used without further purification. MS m/z 854.5 (M+H, expected 853.36 for $C_{46}H_{56}ClN_5O_7Si$).

Preparation 12

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester To a suspension of the product of Preparation 11 in dichloromethane (1.0 mL, 0.3 M) added triethylamine trihydrofluoride (245 µL, 1.5 mmol). This mixture was stirred at room temperature for 45 h and then the mixture was concentrated in vacuo. The residue was dissolved in a mixture of DMF (0.5 mL), acetonitrile/water (1:1, with 0.1% TFA, 0.6 mL), TFA (0.3 mL) and acetonitrile (about 1 mL) and this mixture was purified by prep-RP-HPLC (gradient: 2 to 50% acetonitrile in water with 0.05% TFA). The appropriate fractions were collected and combined and lyophilized to give the ditrifluoroacetate salt of the title compound (100 mg, 34% yield, 98.7% pure by HPLC) as an off-white solid. MS m/z 740.5 (M+H, expected 739.28 for $C_{40}H_{42}ClN_5O_7$).

Example 1

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt A solution of 1,2-ethanedisulfonic acid dihydrate (3.8 mg, 0.02 mmol) in ethanol 0.2 mL) was slowly added to a solution of the product of Preparation 12 (1.4.3 mg, 0.02 mmol) in a 64:1 v/v mixture of isopropanol and dichloromethane (1 mL). The resulting solution was heated at 45° C. to 50° C. for about 30 minutes. The mixture was then slowly cooled to room temperature at which time the solution became slightly cloudy. The solution was allowed to stand at ambient temperature under a gentle stream of nitrogen overnight. The resulting precipitate was collected by filtration and dried to provide the title compound as a white crystalline solid (13 mg, 72% yield).

Example 2

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt A solution of biphenyl-2-ylcarbamic acid 1-[2-(2-chloro-4-{[(r)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester, (26.8 mg, 0.0362 mmol) was prepared in ethanol (5.36 mL) and stirred at room temperature until complete dissolution was obtained (5 min). A solution of 1,2-ethanedisulfonic acid dihydrate (8.2 mg, 0.0362 mmol) in ethanol (0.2 mL) was slowly added to the first solution over approximately one minute. The resulting suspension was stirred for five minutes then isolated by filtration under nitrogen. The resulting precipitate was dried to provide the title compound as a white solid (28.5 mg, 85% yield).

Example 3

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt Biphenyl-2-ylcarbamic acid 1-[2-(2-chloro-4-{[(r)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester (5 g, 6.75 mmol, >99% pure) was dissolved in isopropanol (100 mL), followed by addition of ethane disulfonic acid dihydrate (1.525 mg, 6.75 mmol) dissolved in water (20 mL). The resulting slurry was stirred at room temperature for 1 hour, and then at ~30° C. overnight. The title compound (6.0 g) was isolated as a white powder. The product was heated in 20% water in isopropanol (100 mL) at 30° C. for 48 hours. After cooling to room temperature, the resulting precipitate was isolated by filtration and dried in air for 2 hours to yield the title compound (5.4 g).

Preparation 13

Methyl 4-Acryloylamino-5-chloro-2-methoxybenzoate

To a 1-liter three-necked round-bottom flask equipped with overhead stirrer, temperature control and addition funnel was added methyl 4-amino-5-chloro-2-methoxybenzoate (44.2 g, 200 mmol), dichloromethane (500 mL) and diisopropylethylamine (104.5 mL, 600 mmol). The resulting mixture was stirred at room temperature until the ingredients dissolved and then the mixture was cooled to 0° C. Acryloyl chloride (16.25 mL, 200 mmol) was then added dropwise while maintaining the internal reaction mixture temperature below 10° C. The total time for addition was about 30 min. The reaction mixture was then slowly warmed from 0° C. to room temperature over a period of about 2 hours. Aqueous saturated sodium bicarbonate solution (200 mL) and dichloromethane (200 mL) were then added and this mixture was stirred for 15 min. and then the layers were separated. The dichloromethane layer was washed with 1 M hydrochloric acid (200 mL) and then concentrated under reduced pressure to about one-third its original volume resulting in a thick slurry. The slurry was filtered and the filter cake was washed with dichloromethane (100 mL) and dried to provide the title compound as an off-white solid (36 g, 67% yield, >98% purity by HPLC).

Preparation 14

Methyl 4-{3-[4-(Biphenyl-2-ylcarbamoyloxy)piperidin-1-yl]propionylamino}-5-chloro-2-methoxybenzoate To a 1-liter three-necked round-bottom flask equipped with overhead stirrer, temperature control and reflux condensor was added biphenyl-2-ylcarbamic acid piperidin-4-yl ester (36.3 g, 122 mmol), dichloromethane (500 mL) and isopropanol (100 mL). The resulting mixture was stirred at room temperature until the ingredients dissolved and then the product from Preparation 10 (30 g, 111.5 mmol) was added. Stirring was continued at room temperature until the ingredients dissolved and the mixture was then heated under reflux (50° C. to 55° C.) for 18 hours. The reaction mixture was then cooled to room temperature and ethanol (200 mL) was added. This mixture was concentrated under reduced pressure to a volume of about 150 mL resulting in a thick slurry. The slurry was filtered and the filter cake was washed with ethanol (50 mL) and dried to provide the title compound as a white solid (58 g, 92% yield, 99.5% pure by HPLC).

Preparation 15

Biphenyl-2-ylcarbamic Acid 1-[2-(2-Chloro-4-hydroxymethyl-5-methoxy-phenylcarbamoyl)ethyl]piperidin-4-yl Ester To a 2-liter round-bottom flask was added the product from Preparation 14 (40 g, 70.8 mmol) and THF (400 mL). The resulting mixture was stirred at room temperature until the ingredients dissolved and then the flask was purged with nitrogen for 5 minutes. The mixture was then cooled 0° C. (internal temperature) and a 1 M solution of lithium aluminum hydride in THF (106 mL, 106 mmol) was added dropwise via an additional funnel while maintaining the internal reaction mixture temperature below 10° C. The total addition time was about 40 min. The reaction mixture was then stirred for 1 hour at 0° C. and then 1 M sodium hydroxide (200 mL) was added while maintaining the internal reaction mixture temperature below 15° C. The layers were then separated and the THF layer was washed with aqueous saturated sodium chloride solution (100 mL), dried over sodium sulfate, filtered and concentrated under reduced pressure to provide the title compound as a white solid (38 g, 100% yield, 94% purity by HPLC).

Preparation 16

Biphenyl-2-ylcarbamic Acid 1-[2-(2-Chloro-4-formyl-5-methoxyphenyl-carbamoyl)ethyl]piperidin-4-yl Ester To a 1-liter round-bottom flask was added the product from Preparation 15 (28 g, 52 mmol) and dichloromethane (500 mL). The resulting mixture was stirred at room temperature until the ingredients dissolved and then activated manganese (IV) oxide (45 g, 520 mmol) was added. The reaction mixture was stirred at room temperature under nitrogen for 12 hours and then filtered through a pad of Celite. The mixture was then concentrated under reduced pressure and the residue was dried overnight under vacuum to provide the title compound as a yellow solid (26 g, 93% yield, about 93% purity by HPLC).

Preparation 17

Biphenyl-2-ylcarbamic Acid 1-[2-(4-{[(R)-2-(tert-Butyldimethylsilanyloxy)-2-(8-hydroxy-2-oxo-1,2-dihydroquinolin-5-yl)ethylamino]methyl}-2-chloro-5-methoxy-phenylcarbamoyl)ethyl]piperidin-4-yl Ester To a 500 mL round-bottom flask was added the product from Preparation 16 (6 g, 11.2 mmol) and dichloromethane (50 mL). The resulting mixture was stirred at room temperature until the ingredients dissolved and then the product of Preparation 7 (6 g, 15.0 mmol) and dry methanol (50 mL) were added. This mixture was stirred at room temperature under nitrogen for 2 hours (clear yellow to orange solution) and then the mixture was cooled to 0 to 5° C. Solid sodium triacetoxyborohydride (7.2 g, 34 mmol) was added in portions over a 10 minute period and then the reaction mixture was slowly warmed from 0° C. to room temperature over a period of about 2 hours. The mixture was then cooled to 0° C. and 1 M aqueous sodium hydroxide solution (50 mL) and dichloromethane 150 mL) were added. The mixture was stirred thoroughly and then the layers were separated. The organic layer was washed with aqueous saturated sodium chloride solution (50 mL), filtered, dried over sodium sulfite, filtered and concentrated under reduced pressure to give the title compound as a yellow solid (10.1 g, 100% yield, 87% purity by HPLC).

Example 4

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt To a 50 mL round-bottom flask was added the product from Preparation 17 (2.0 g, 2.5 mmol) and dichloromethane (10 mL). The resulting mixture was stirred at room temperature until the ingredients dissolved and then triethylamine trihydrofluoride (1.2 mL, 7.5 mmol) was added and the resulting mixture was stirred at 25° C. for 20 hours. A solution of 1,2-ethanedisulfonic acid dihydrate (0.56 g, 2.5 mmol) in methanol (10 mL) was then added and this mixture was stirred at 30° C. for 2 hours at which time a thick white slurry had formed. The slurry was filtered slowly and the filter cake was washed with methanol (10 mL), air dried for 2 hours and then dried overnight under vacuum to provide the title compound as a fine white powder (1.5 g, >98% purity by HPLC).

Example 5

Purification of Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt To biphenyl-2-ylcarbamic acid 1-[2-(2-chloro-4-{[(R)-2-hydroxy-2-(8-hydroxy-2-oxo-1,2-dihydroquinolin-5-yl) ethylamino]methyl}-5-methoxyphenylcarbamoyl)-ethyl]piperidin-4-yl ester 1,2-ethanedisulfonic acid salt, prepared as in Example 4 (80 g) was added a solution of 20% water in isopropanol by volume (800 mL). The resulting slurry was left at room temperature overnight and then filtered to provide the title compound having improved crystallinity and purity (74 g).

Preparation 18

Seed Crystals of Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt Step (a)
Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester 1,2-ethanedisulfonic acid salt, prepared as in Example 4 (100 mg) was dissolved in 13% water in methanol (20 mL) at ~60° C. The resulting clear solution was allowed to cool to room temperature in a closed container. After 48 hours, the resulting plate-like crystals were isolated by filtration.

Step (b)

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester 1,2-ethanedisulfonic acid salt, prepared as in Example 4 (1.0 g) was dissolved in 15% water in methanol (100 mL) at 60-65° C. The clear, stirred solution was allowed to cool to 30° C., and then the crystalline product of Step (a) (4.2 mg) was added. The solution was cooled to 20° C. and stirred for 2 hours. The resulting precipitate was isolated by filtration and dried in air for 1 hour to provide the title compound (680 mg).

Step (c)

The procedure of Step (b) was repeated substituting the product of Step (b) (20 mg) for the product of step (a), to provide the title compound (690 mg).

Step (d)

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester 1,2-ethanedisulfonic acid salt, prepared as in Example 4 (10 g) was dissolved in 15% water in methanol (1 L) at 60-65° C. The clear, stirred solution was allowed to cool to 30° C., and then the crystalline product of step (c) (4.2 mg) was added. The solution was cooled to 20° C. and stirred for 18 hours. The resulting precipitate was isolated by filtration and dried in air for 2 hours to provide the title compound (5.5 g).

Example 6

Recrystallization of Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1,2-Ethanedisulfonic Acid Salt Using Seed Crystals To a 12 L round-bottom flask was added the product from Example 5 (60 g, 64.5 mmol), water (0.9 L) and methanol (5.1 L). The resulting mixture was heated from 25° C. to 61-65° C. with stirring until the ingredients dissolved and stirred for an additional 20 minutes at 60-65° C. The mixture was allowed to cool to 30° C. and then the product of Preparation 18 (2 g, 2.15 mmol) was added. This mixture was slowly cooled to 20° C. and the resulting slurry was stirred for an additional 2 hours at 30° C. The product was filtered with methanol (500 mL) and dried in air for 2 hours and then in vacuo at 25-30° C. for 18 hours to provide the title compound (43 g, 72% yield, 99.2% purity).

Example 7

Thermal Analysis

Figure 2:
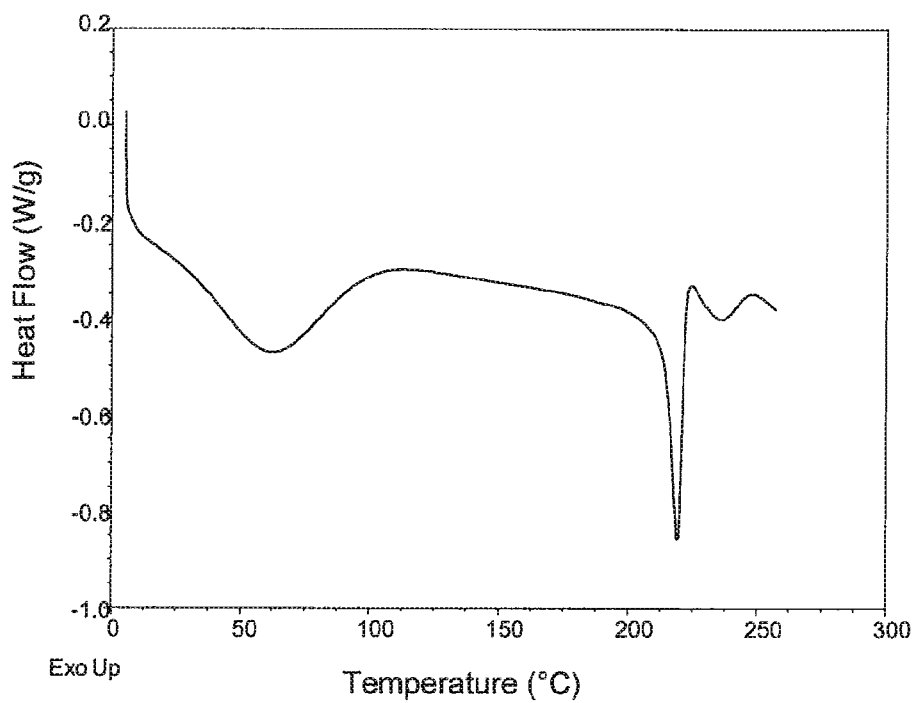

Differential scanning calorimetry (DSC) was performed using a TA Instruments Model Q-10 module with a Thermal Analyst controller. Data were collected and analyzed using TA Instruments Thermal Solutions software. A sample of about 1 mg was accurately weighed into an aluminum pan with lid. The sample was evaluated using a linear heating ramp of 5° C./min from ambient temperature to approximately 300° C. The DSC cell was purged with dry nitrogen during use. A representative DSC trace for a sample of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of Example 6 is shown in FIG. 1 and a representative DSC trace for a sample of Example 2 is shown in FIG. 2.

Thermogravimetric analysis (TGA) was performed using a TA Instruments Model Q-50 module equipped with high resolution capability. Data were collected and analyzed using TA Instruments Thermal Solutions software. A sample weighing about 10 mg was placed onto a platinum pan and scanned with a high resolution-heating rate from ambient temperature to 300° C. The balance and furnace chambers were purged with nitrogen flows during use. A representative TGA trace for a sample of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of Example 6 is shown in FIG. 1.

The DSC traces demonstrate that a 1,2-ethanedisulfonic acid salt of the present invention has excellent thermal stability with melting points at about 239° C. and at about 219° C., respectively, and no thermal decomposition below about 200° C.

Example 8

Powder X-Ray Diffraction

Powder x-ray diffraction patterns were obtained with a Thermo ARL X-Ray Diffractometer Model X'TRA (Thermo ARL SA, Switzerland) using Cu Kα radiation at 1.542 Å (45 kV, 40 mA) with a Si(Li) solid-state detector. The analysis was typically performed at a scan rate of 2°/min with a step size of 0.03° per point over a range of 2 to 30° in two-theta angle. Samples, either as received or ground to a fine powder, were gently packed into a custom small-volume insert designed to fit into the instrument top-loading sample cup for analysis. The instrument was calibrated weekly to a silicon metal standard, within ±0.02° two-theta angle. A representative PXRD patterns for a sample of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of Example 6 is shown in FIG. 3 and the pattern for a sample of Example 2 is shown in FIG. 4.

Example 9

Infrared Analysis

The infrared (IR) absorption spectrum was determined over the frequency range 4000 to 675 cm$^{-1}$ using an Avatar 360 FT-IR spectrometer equipped with a Nicolet attenuated total reflection (ATR) sample holder. A representative IR absorption spectrum for a sample of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester for a sample of Example 6 had significant absorption bands at 704±1, 748±1, 768±1, 841±1, 900±1, 1055±1, 1104±1, 1166±1, 1218±1, 1294±1, 1408±1, 1522±1, 1609±1, 1655±1, and 1701±1, as illustrated in FIG. 5.

Example 10

Dynamic Moisture Sorption Assessment

Figure 6:
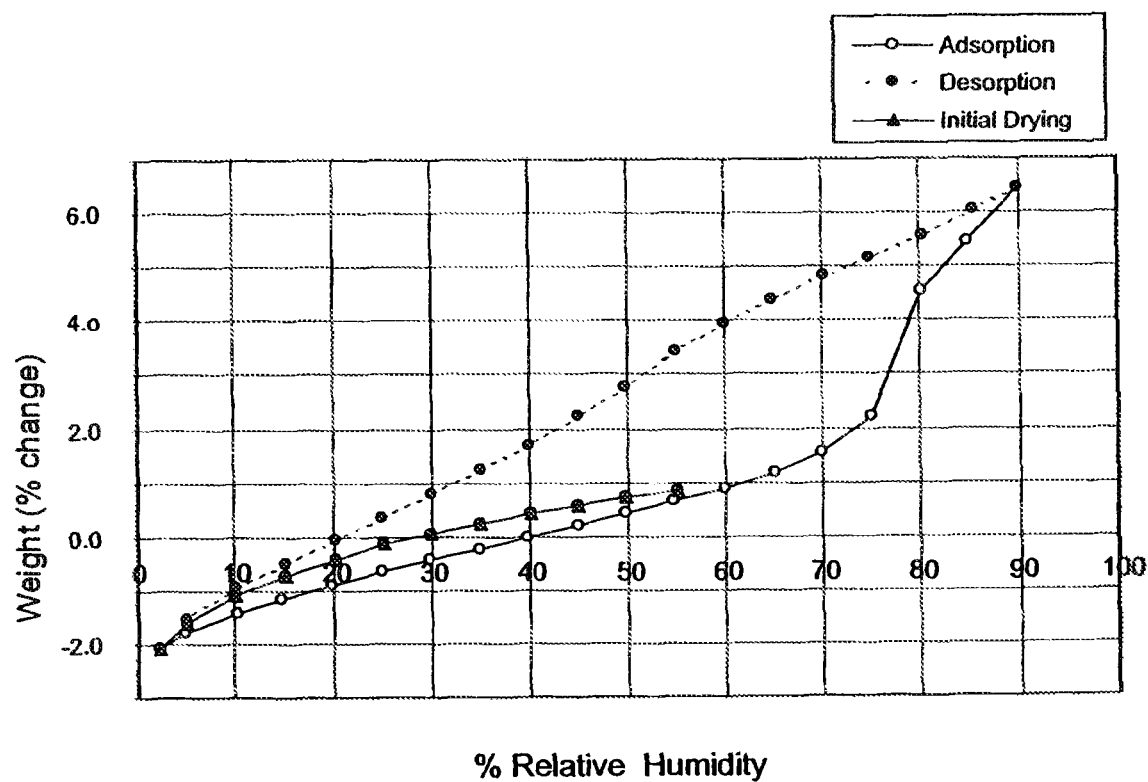
FIG. 6 shows a dynamic moisture sorption (DMS) trace for a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention.

A dynamic moisture sorption (DMS) assessment (also known as a moisture sorption-desorption profile) was performed for a hand ground sample of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of Preparation 18 using VTI atmospheric microbalance, SGA-100 system (VTI Corp., Hialeah, Fla. 33016), A sample size of approximately 10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (+/−5% RH) when the mass of the sample was stable to within 0.01% for 5 consecutive points. A representative DMS trace is shown in FIG. 6.

The DMS trace demonstrates that a 1,2-ethanedisulfonic acid salt of the present invention has a reversible sorption/desorption profile with moderate (<9%) hygroscopicity, The salt has less than 2.5% weight gain in the humidity range of 40% RH to 75% RH. The reversible moisture sorption/desorption profile demonstrates that a crystalline salt of the present invention possesses an acceptable hygroscopicity and is not deliquescent.

Example 11

Elemental Analysis and Counterion Ratio

The following elemental percentages of carbon, hydrogen, nitrogen, and sulfur of a sample of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of Example 6 were determined by combustion analysis using a Flash EA 1112 Elemental Analyzer (GE Elantech, Lakewood, N.J.): carbon 52.95%, hydrogen 5.43%, nitrogen 6.83%, and sulfur 6.87%. The weight percentage of 1,2-ethanedisulfonic acid in the crystalline sample, calculated from the measured weight percentage of sulfur, is 20.4%, which is equal to the theoretical weight percentage of 20.4%, providing a counterion ratio of 1:1.

Preparation A

Cell Culture and Membrane Preparation from Cells Expressing Human $\beta_1$, $\beta_2$ or $\beta_3$ Adrenergic Receptors Chinese hamster ovarian (CHO) cell lines stably expressing cloned human $\beta_1$, $\beta_2$ or $\beta_3$ adrenergic receptors, respectively, were grown to near confluency in Hams F-12 media with 10% FBS in the presence of 500 μg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use. For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice. For the more protease-sensitive $\beta_3$ receptor expressing membranes, cell pellets were homogenated lysis buffer (10 mM Tris/HCl, pH 7.4) supplemented with one tablet of "Complete Protease Inhibitor Cocktail Tablets with 2 mM EDTA" per 50 mL buffer (Roche Catalog No. 1697498, Roche Molecular Biochemicals, Indianapolis, Ind.). The homogenate was centrifuged at 20,000×g, and the resulting pellet was washed once with lysis buffer by re-suspension and centrifugation as above. The final pellet was then re-suspended in ice-cold binding assay buffer (75 mM Tris/HCl pH 7.4, 12.5 mM MgCl$_2$, 1 mM EDTA). The protein concentration of the membrane suspension was determined by the methods described in Lowry et al., 1951, *Journal of Biological Chemistry*, 193, 265; and Bradford, *Analytical Biochemistry*, 1976, 72, 248-54. All membranes were stored frozen in aliquots at −80° C. or used immediately.

Preparation B

Cell Culture and Membrane Preparation from Cells Expressing Human $M_1$, $M_2$, $M_3$ and $M_4$ Muscarinic Receptors CHO cell lines stably expressing cloned human hM$_1$, hM$_2$, hM$_3$ and hM$_4$ muscarinic receptor subtypes, respectively, were grown to near confluency in HAM's F-12 media supplemented with 10% FBS and 250 μg/mL Geneticin. The cells were grown in a 5% CO$_2$, 37° C. incubator and lifted with 2 mM EDTA in dPBS. Cells were collected by 5 minute centrifugation at 650×g, and cell pellets were either stored frozen at −80° C. or membranes were prepared immediately for use. For membrane preparation, cell pellets were resuspended in lysis buffer and homogenized with a Polytron PT-2100 tissue disrupter (Kinematica AG; 20 seconds×2 bursts), Crude membranes were centrifuged at 40,000×g for 15 minutes at 4° C. The membrane pellet was then resuspended with re-suspension buffer and homogenized again with the Polytron tissue disrupter. The protein concentration of the membrane suspension was determined by the method described in Lowry et al., 1951, *Journal of Biochemistry*, 193, 265. All membranes were stored frozen in aliquots at −80° C. or used immediately. Aliquots of prepared hM$_5$ receptor membranes were purchased directly from Perkin Elmer and stored at −80° C. until use.

Assay Test Procedure A

Radioligand Binding Assay for Human $\beta_1$, $\beta_2$ and $\beta_3$ Adrenergic Receptors Binding assays were performed in 96-well microtiter plates in a total assay volume of 100 μL with 10-15 μg of membrane protein containing the human $\beta_1$, $\beta_2$ or $\beta_3$ adrenergic receptors in assay buffer (75 mM Tris/HCl pH 7.4 at 25° C., 12.5 mM MgCl$_2$, 1 mM EDTA, 0.2% BSA). Saturation binding studies for determination of K$_d$ values of the radioligand were done using [$^3$H]-dihydroalprenolol (NET-720, 100 Ci/mmol, PerkinElmer Life Sciences Inc., Boston, Mass.) for the $\beta_1$ and $\beta_2$ receptors and [$^{125}$I]-(−)-iodocyanopindolol (NEX-189, 220 Ci/mmol, PerkinElmer Life Sciences Inc., Boston, Mass.) at 10 or 11 different concentrations ranging from 0.01 nM to 20 nM. Displacement assays for determination of K$_i$ values of test compounds were done with [$^3$H]-dihydroalprenolol at 1 nM and [$^{125}$I]-(−)-iodocyanopindolol at 0.5 nM for 10 or 11 different concentrations of test compound ranging from 10 pM to 10 μM. Non-specific binding was determined in the presence of 10 μM propranolol. Assays were incubated for 1 hour at 37° C., and then binding reactions were terminated by rapid filtration over GF/B for the $\beta_1$ and $\beta_2$ receptors or GF/C glass fiber filter plates for the $\beta_3$ receptors (Packard BioScience Co., Meriden, Conn.) pre-soaked in 0.3% polyethyleneimine. Filter plates were washed three times with filtration buffer (75 mM Tris/HCl pH 7.4 at 4° C., 12.5 mM $MgCl_2$, 1 mM EDTA) to remove unbound radioactivity. The plates were then dried and 50 μL of Microscint-20 liquid scintillation fluid (Packard BioScience Co., Meriden, Conn.) was added and plates were counted in a Packard Topcount liquid scintillation counter (Packard BioScience Co., Meriden, Conn.), Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM propranolol. $K_i$ values for test compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099-108).

In this assay, a lower $K_i$ value indicates that a test compound has a higher binding affinity for the receptor tested, When tested in this assay, the compound of formula I was found to have a $K_i$ value of less than 10 nM for the human $\beta_2$ adrenergic receptor.

Assay Test Procedure B

Radioligand Binding Assay for Muscarinic Receptors

Radioligand binding assays for cloned human muscarinic receptors were performed in 96-well microtiter plates in a total assay volume of 100 μL. CHO cell membranes stably expressing either the $hM_1$, $hM_2$, $hM_3$, $hM_4$ or $hM_5$ muscarinic subtype were diluted in assay buffer to the following specific target protein concentrations (μg/well): 10 μg for $hM_1$, 10-15 μg for $hM_2$, 10-20 μg for $hM_3$, 10-20 μg for $hM_4$, and 10-12 μg for $hM_5$ to get similar signals (cpm). The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL, diluted test compound, and 50 μL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. The plates were then air dried and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23):3099-108). $K_i$ values were converted to p$K_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. When tested in this assay, the compound of formula I was found to have a $K_i$ value of less than 10 nM for the human $M_2$ and $M_3$ muscarinic receptors.

Assay Test Procedure C

Whole-Cell cAMP Flashplate Assay in CHO Cell Lines Heterologously Expressing Human $\beta_1$, $\beta_2$ or $\beta_3$ Adrenergic Receptors cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. For the determination of β receptor agonist potency ($EC_{50}$), CHO-K1 cell lines stably expressing cloned human $\beta_1$, $\beta_2$ or $\beta_3$ adrenergic receptors were grown to near confluency in HAM's F-12 media supplemented with 10% FBS and Geneticin (250 μg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing IBMX (PerkinElmer Kit) pre-warmed to room temperature to a concentration of 1.6×10$^6$ to 2.8×10$^6$ cells/mL. About 60,000 to 80,000 cells per well were used in this assay. Test compounds (10 mM DMSO) were diluted into PBS containing 0.1% BSA in Beckman Biomek-2000 and tested at 11 different concentrations ranging from 100 μM to 1 pM. Reactions were incubated for 10 min at 37° C. and stopped by adding 100 μL of cold detection buffer containing [$^{125}$I]-cAMP (NEN SMP004, PerkinElmer Life Sciences, Boston, Mass.). The amount of cAMP produced (pmol/well) was calculated based on the counts observed for the samples and cAMP standards as described in the manufacturer's user manual. Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology*, 1973, 22, 23, 3099-108) was used to calculate the EC50 values.

In this assay, a lower $EC_{50}$ value indicates that the test compound has a higher functional activity at the receptor tested. When tested in this assay, the compound of formula I was found to have an $EC_{50}$ value of less than 10 nM for the human $\beta_2$ adrenergic receptor.

Assay Test Procedure D

Functional Assays of Antagonism for Muscarinic Receptor Subtypes

A. Blockade of Agonist-Mediated [$^{35}$S]GTPγS Binding

The functional potency of a test compound was determined by measuring the ability of the compound to block oxotremorine-stimulated [$^{35}$S]GTPγS binding in CHO-K1 cells expressing the $hM_2$ receptor.

At the time of use, frozen membranes were thawed and then diluted in assay buffer with a final target tissue concentration of 5-10 μg protein per well. The membranes were briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 μL of assay buffer with [$^{35}$S]GTPγS (0.4 nM), 25 μL of oxotremorine ($EC_{90}$) and GDP (3 uM), 25 μL of diluted test compound and 25 μL CHO cell membranes expressing the $hM_2$ receptor. The assay plates were then incubated at 37° C. for 60 minutes. The assay plates were filtered over 1% BSA-pretreated GF/B filters using a PerkinEimer 96-well harvester. The plates were rinsed with ice-cold wash buffer for 3×3 seconds and then air or vacuum dried. Microscint-20 scintillation liquid (50 μL) was added to each well, and each plate was seated and radioactivity counted on a Topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. When tested in this assay, the compound of formula I was found to have a $K_i$ value of less than about 10 nM for blockade of oxotremorine-stimulated [$^{35}$S]GTPγS binding in CHO-K1 cells expressing the $hM_2$ receptor.

B. Blockade of Agonist-Mediated Calcium Release Via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium.

For FLIPR calcium stimulation assays, CHO cells stably expressing the $hM_1$, $hM_3$ and $cM_5$ receptors were seeded into 96-well FLIPR plates the night before the assay was done. Seeded cells were washed twice by Cellwash (MTX Labsystems, Inc.) with FLIPR buffer (10 mM HEPES, pH 7.4, 2 mM calcium chloride, 2.5 mM probenecid in Hank's Buffered Salt Solution (HBSS) without calcium and magnesium) to remove growth media and leaving 50 μL/well of FLIPR buffer. The cells were then incubated with 50 μL/well of 4 μM FLUO-4AM (a 2× solution was made) for 40 minutes at 37° C., 5% carbon dioxide. Following the dye incubation period, cells were washed two times with FLIPR buffer, leaving a final volume of 50 μL/well.

To determine antagonist potency, the dose-dependent stimulation of intracellular $Ca^{2+}$ release for oxotremorine was first determined so that antagonist potency can later be measured against oxotremorine stimulation at an $EC_{90}$ concentration. Cells were first incubated with compound dilution buffer for 20 minutes, followed by agonist addition, which was performed by the FLIPR. An $EC_{90}$ value for oxotremorine was generated according to the method detailed in the FLIPR measurement and data reduction section below, in conjunction with the formula $EC_F=((F/100-F)^\wedge 1/H)*EC_{50}$. An oxotremorine concentration of $3\times EC_F$ was prepared in stimulation plates such that an $EC_{90}$ concentration of oxotremorine was added to each well in the antagonist inhibition assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence was expressed as maximum fluorescence minus baseline fluorescence for each well. The raw data was analyzed against the logarithm of drug concentration by nonlinear regression with GraphPad Prism (GraphPad Software, Inc., San Diego, Calif.) using the built-in model for sigmoidal dose-response. Antagonist $K_i$ values were determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. When tested in this assay, the compound of formula I was found to have a $K_i$ value of less than about 10 nM for blockade of agonist-mediated calcium release in CHO cells stably expressing the $hM_1$, hM3 and $cM_5$ receptors.

Assay Test Procedure E

Whole-Cell cAMP Flashplate Assay with a Lung Epithelial Cell Line Endogenously Expressing Human $β_2$ Adrenergic Receptor For the determination of agonist potencies and efficacies (intrinsic activities) in a cell line expressing endogenous levels of the $β_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat #181-500, Biosource International, Camarillo, Calif.). The day before the assay, medium was switched to LHC-8 (no epinephrine or retinoic acid, cat #141-500, Biosource International, Camarillo, Calif.).

cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and re-suspended in stimulation buffer pre-warmed to 37° C. at a final concentration of 600,000 cells/mL. Cells were used at a final concentration of 100,000 to 120,000 cells/well in this assay. Test compounds were serially diluted into assay butler (75 mM Tris/HCl pH 7.4 at 25° C., 12.5 mM $MgCl_2$, 1 mM EDTA, 0.2% BSA) in Beckman Biomek-2000. Test compounds were tested in the assay at 11 different concentrations, ranging from 10 µM to 10 pM. Reactions were incubated for 10 min at 37° C. and stopped by addition of 100 µL of ice-cold detection buffer. Plates were sealed, incubated over night at 4° C. and counted the next morning in a Topcount scintillation counter (Packard BioScience Co., Meriden, Conn.). The amount of cAMP produced per of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response.

In this assay, a lower $EC_{50}$ value indicates that the test compound has a higher functional activity at the receptor tested. When tested in this assay, the compound of formula I was found to have an $EC_{50}$ value of less than about 10 nM for the $\beta_2$ adrenergic receptor.

Assay Test Procedure F

Duration Bronchoprotection in Guinea Models of Acetylcholine-Induced or Histamine-Induced Bronchoconstriction These in viva assays were used to assess the bronchoprotective effects of test compounds exhibiting both muscarinic receptor antagonist and $\beta_2$ adrenergic receptor agonist activity. To isolate muscarinic antagonist activity in the acetylcholine-induced bronchoconstriction model, the animals were administered propanolol, a compound that blocks β receptor activity, prior to the administration of acetylcholine. Duration of bronchoprotection in the histamine-induced bronchoconstriction model reflects $\beta_2$ adrenergic receptor agonist activity.

Groups of 6 male guinea pigs (Duncan-Hartley (HsdPoc: DH) Harlan, Madison, Wis.) weighing between 250 and 350 g were individually identified by cage cards. Throughout the study, animals were allowed access to food and water ad libitum.

Test compounds were administered via, inhalation over 10 minutes in a whole-body exposure dosing chamber (R&S Molds, San Carlos, Calif.). The dosing chambers were arranged so that an aerosol was simultaneously delivered to 6 individual chambers from a central manifold. Guinea pigs were exposed to an aerosol of a test compound or vehicle (WFI). These aerosols were generated from aqueous solutions using an LC Star Nebulizer Set (Model 22F51, PARI Respiratory Equipment, Inc, Midlothian, Va.) driven by a mixture of gases ($CO_2=5\%$, $O_2=21\%$ and $N_2=74\%$) at a pressure of 22 psi. The gas flow through the nebutizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This value was measured gravimetrically by comparing pre- and post-nebulization weights of the filled nebulizer.

The bronchoprotective effects of test compounds administered via inhalation were evaluated using whole body plethysmography at 1.5, 24, 48 and 72 hours post-dose.

Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-3 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of acetylcholine (Ach) or histamine in saline. The trachea was then dissected free and cannulated with a 14G teflon tube (#NE-014, Small Parts, Miami Lakes, Fla.). If required, anesthesia was maintained by additional intramuscular injections of the aforementioned anesthetic mixture. The depth of anesthesia was monitored and adjusted if the animal responds to pinching of its paw or if the respiration rate was greater than 100 breaths/minute.

Once the cannulations were completed, the animal was placed into a plethysmograph (#PLY3114, Buxco Electronics, Inc., Sharon, Conn.) and an esophageal pressure cannula (PE-160, Becton Dickinson, Sparks, Md.) was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways did not collapse and that the animal did not suffer from hyperventilation.

Once it was determined that baseline values were within the range of 0.3-0.9 mL/cm $H_2O$ for compliance and within the range of 0.1-0199 cm $H_2O$/mL per second for resistance, the pulmonary evaluation was initiated. A Buxco pulmonary measurement computer program enabled the collection and derivation of pulmonary values.

Starting this program initiated the experimental protocol and data collection. The changes in volume over time that occur within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach or histamine. When evaluating the muscarinic antagonist effects, propanolol (5 mg/Kg, iv) (Sigma-Aldrich, St, Louis, Mo.) was administered 15 minutes prior to challenge with Ach. Ach (Sigma-Aldrich, St. Louis, Mo.) (0.1 mg/mL) was infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. Alternatively, bronchoprotection of test compounds was assessed in the acetylcholine challenge model without pretreatment with a beta blocking compound.

When evaluating the $\beta_2$ adrenergic receptor agonist effects of test compounds, histamine (25 µg/mL) (Sigma-Aldrich, St. Louis, Mo.) was infused intravenously for 1 minute from a syringe pump at the following doses and prescribed times from the start of the experiment: 0.5 µg/minute at 5 minutes, 0.9 µg/minute at 10 minutes, 1.9 µg/minute at 15 minutes, 3.8 µg/minute at 20 minutes, 7.5 µg/minute at 25 minutes and 15

μg/minute at 30 minutes. If resistance or compliance had not returned to baseline values at 3 minutes following each Ach or histamine dose, the guinea pig's lungs were inflated 3 times with 4 mL of air from a 10 mL calibration syringe. Recorded pulmonary parameters include respiration frequency (breaths/minute), compliance (mL/cm $H_2O$) and pulmonary resistance (cm $H_2O$/mL per second). Once the pulmonary function measurements were completed at minute 35 of this protocol, the guinea pig was removed from the plethysmograph and euthanized by carbon dioxide asphyxiation.

The data were evaluated in one of two ways:

(a) Pulmonary resistance ($R_L$, cm $H_2O$/mL per second) was calculated from the ratio of "change in pressure" to "the change in flow." The $R_L$ response to ACh (60 μg/min, IH) was computed for the vehicle and the test compound groups. The mean ACh response in vehicle-treated animals, at each pre-treatment time, was calculated and used to compute % inhibition of ACh response, at the corresponding pre-treatment time, at each test compound dose. Inhibition dose-response curves for '$R_L$' were fitted with a four parameter logistic equation using GraphPad Prism, version 3.00 for Windows (GraphPad Software, San Diego, Calif.) to estimate bronchoprotective $ID_{50}$ (dose required to inhibit the ACh (60 μg/min) bronchocontrictor response by 50%). The equation used was as follows:

$$Y = \text{Min} + (\text{Max} - \text{Min})/(1 + 10^{((\log ID50 - X) * Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of Ach or histamine needed to cause a doubling of the baseline pulmonary resistance, was calculated using the pulmonary resistance values derived from the flow and the pressure over a range of Ach or histamine challenges using the following equation (derived from the equation used to calculate $PC_{20}$ values in the clinic (see *Am. Thoracic Sac*, 2000):

$$PD_2 = \text{antilog}\left[\log C_1 + \frac{(\log C_2 - \log C_1)(2R_0 - R_1)}{R_2 - R_1}\right]$$

where:
$C_1$ = concentration of Ach or histamine preceding $C_2$
$C_2$ = concentration of Ach or histamine resulting in at least a 2-fold increase in pulmonary resistance ($R_L$)
$R_0$ = Baseline $R_L$ value
$R_1 = R_L$ value after $C_1$
$R_2 = R_L$ value after $C_2$ Statistical analysis of the data was performed using a two tailed—Students t-test. A P-value<0.05 was considered significant.

When tested in this assay, the compound of formula I produced a dose-dependent bronchoprotective effect against MCh-induced bronchoconstriction and His-induced bronchoconstriction. Additionally, the compound of formula I had a duration (PD $T_{1/2}$) of bronchoprotective activity of at least about 24 hours in this assay.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A process for preparing a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester; the process comprising contacting biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester with 1,2-ethanedisulfonic acid or a hydrate thereof.

2. A process for preparing a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, the process comprising:

(a) contacting a compound of formula II:

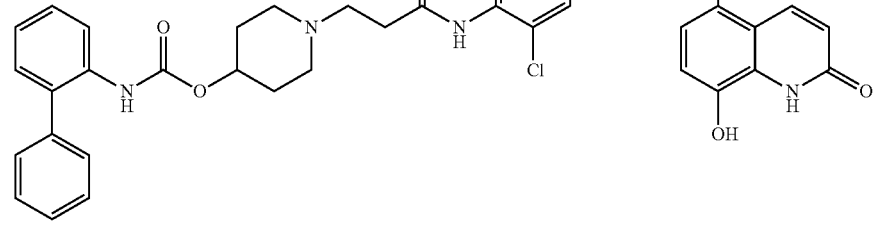

wherein $R^{1a}$, $R^{1b}$ and $R^{1c}$ are independently selected from $C_{1-4}$ alkyl, phenyl, —$C_{1-4}$ alkyl-(phenyl), or one of $R^{1a}$, $R^{1b}$ and $R^{1c}$ is —O—($C_{1-4}$ alkyl); with fluoride ion; and (b) contacting the product from step (a) with 1,2-ethanedisulfonic acid or a hydrate thereof; to form a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, wherein step (a) and (b) are conducted in the same reaction vessel without isolation of the product of step (a).

3. A process for preparing a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]-piperidin-4-yl ester having a melting point greater than about 230° C., the process comprising adding a seed crystal of a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester to a solution comprising a 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester dissolved in an inert diluent, wherein the seed crystal has a melting point greater than about 230° C.

4. A process for preparing a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester having a melting point greater than about 230° C., the process comprising:
(a) dissolving a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester in an inert diluent at a first temperature;
(b) cooling the product of step (a) to a second temperature; and
(c) adding a seed crystal of 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester;
wherein:
(i) the seed crystal has a melting point higher than about 230° C.,
(ii) the first temperature is a temperature sufficient to dissolve the 1,2-ethanedisulfonic acid salt, and
(iii) the second temperature is below a temperature at which the seed crystal completely dissolves when added to the product of step (b).

5. A process for purifying biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester; the process comprising forming a crystalline 1,2-ethanedisulfonic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester by contacting the biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester with 1,2-ethanedisulfonic acid or a hydrate thereof.

* * * * *